(12) United States Patent
Landfield et al.

(10) Patent No.: US 9,464,322 B2
(45) Date of Patent: Oct. 11, 2016

(54) METHODS FOR DIAGNOSING AND TREATING ALZHEIMER'S DISEASE (AD) USING THE MOLECULES THAT STABILIZE INTRACELLULAR CALCIUM ($CA_{2+}$) RELEASE

(75) Inventors: Philip W. Landfield, Lexington, KY (US); John Christopher Gant, Lexington, KY (US); Eric M. Blalock, Lexington, KY (US); Kuey-Chu Chen, Lexington, KY (US); Olivier Thibault, Lexington, KY (US); Nada Porter, Lexington, KY (US)

(73) Assignee: UNIVERSITY OF KENTUCKY RESEARCH FOUNDATION, Lexington, KY (US)

( * ) Notice: Subject to any disclaimer, the term of this patent is extended or adjusted under 35 U.S.C. 154(b) by 0 days.

(21) Appl. No.: 13/608,596

(22) Filed: Sep. 10, 2012

(65) Prior Publication Data

US 2013/0123188 A1   May 16, 2013

Related U.S. Application Data

(60) Provisional application No. 61/533,056, filed on Sep. 9, 2011.

(51) Int. Cl.
| | |
|---|---|
| *A61K 48/00* | (2006.01) |
| *C12Q 1/68* | (2006.01) |
| *A61K 38/17* | (2006.01) |
| *A61K 38/52* | (2006.01) |

(52) U.S. Cl.
CPC ......... *C12Q 1/6883* (2013.01); *A61K 38/1709* (2013.01); *A61K 38/1738* (2013.01); *A61K 38/52* (2013.01); *C12Y 502/01008* (2013.01); *C12Q 2600/158* (2013.01)

(58) Field of Classification Search
CPC ............... A61K 38/1738; A61K 38/1709; A61K 38/52; C12Q 2600/158; C12Q 1/6883
See application file for complete search history.

(56) References Cited

U.S. PATENT DOCUMENTS

| | | | |
|---|---|---|---|
| 7,879,840 B2 | 2/2011 | Marks et al. | |
| 8,022,058 B2 | 9/2011 | Marks et al. | |
| 2006/0194767 A1 | 8/2006 | Marks et al. | |
| 2006/0293266 A1 | 12/2006 | Marks | |
| 2007/0049572 A1 | 3/2007 | Marks et al. | |
| 2007/0173482 A1 | 7/2007 | Marks et al. | |
| 2010/0196355 A1* | 8/2010 | Graziani et al. | 424/130.1 |
| 2011/0172190 A1 | 7/2011 | Marks et al. | |

OTHER PUBLICATIONS

Smith et al. "Calcium dysregulation in Alzheimer's disease: Recent advances gained from genetically modified animals." Cell Calcium (2005) 38: pp. 427-437.*
Kelliher et al. "Alterations in the ryanodine receptor calcium release channel correlate with Alzheimer's disease neurofibrillary and beta-amyloid pathologies." Neuroscience. (1999);92(2): pp. 499-513.*
NCBI "FKBP1A FK506 binding protein 1A, 12kDa." Website accessed Apr. 11, 2014.*
Bowers et al. "Genetic therapy for the nervous system." Hum Mol Genet. Apr. 15, 2011;20(R1):R28-41.*
Sinn et al. "Gene therapy progress and prospects: development of improved lentiviral and retroviral vectors—design, biosafety, and production." Gene Ther. Jul. 2005;12(14):1089-98.*
Schubert et al. "Gene Delivery to the Nervous System: NINDS Workshop on Gene Delivery to the Nervous System." Molecular therapy : the journal of the American Society of Gene Therapy. 2008;16(4):640-646.*
Nobre and Almeida."Gene therapy for Parkinson's and Alzheimer's diseases: from the bench to clinical trials." Curr Pharm Des. 2011;17(31):3434-45.*
Davidson et al. "Viral vectors for gene delivery to the nervous system." Nat Rev Neurosci. May 2003;4(5):353-64.*
Sanokawa-Akakura et al. "Control of Alzheimer's Amyloid Beta Toxicity by the High Molecular Weight Immunophilin FKBP52 and Copper Homeostasis in *Drosophila*." PLoS ONE (2010) 5(1): pp. 1-10.*
Perrin et al."Multi-modal techniques for diagnosis and prognosis of Alzheimer's disease." Nature. 2009;461(7266):916-922.*
Gorelick PB. "Risk factors for vascular dementia and Alzheimer disease." Stroke. Nov. 2004;35(11 Suppl 1):2620-2. Epub Sep. 16, 2004.*
Bassett et al. "Familial risk for Alzheimer's disease alters fMRI activation patterns." Brain : a journal of neurology.2006;129(Pt 5):1229-1239.*
Lindsay et al. "Risk factors for Alzheimer's disease: a prospective analysis from the Canadian Study of Health and Aging." Am J Epidemiol. Sep. 1, 2002;156(5):445-53.*
Bromley-Brits et al. "Morris water maze test for learning and memory deficits in Alzheimer's disease model mice." J Vis Exp. Jul. 20, 2011;(53). pii: 2920.*
Guo et al. "Protein tolerance to random amino acid change." Proc Natl Acad Sci U S A. Jun. 22, 2004;101(25):9205-10.*
Lesk et al. "How different amino acid sequences determine similar protein structures: the structure and evolutionary dynamics of the globins." J Mol Biol. Jan. 25, 1980;136(3):225-70.*

(Continued)

*Primary Examiner* — Thaian N Ton
*Assistant Examiner* — Titilayo Moloye
(74) *Attorney, Agent, or Firm* — McDermott Will & Emery LLP

(57) ABSTRACT

The subject technology relates, in part, to a method of treating Alzheimer's Disease (AD), early-stage AD, elevated risk of AD, mild cognitive impairment (MCI), or other forms of age-related cognitive decline in a subject in need thereof by administering to the subject a molecule that promotes calcium-release stabilization in ryanodine receptors (RyRs) and/or inosital triphosphate receptors (InsP3Rs) in brain cells. Diagnostic methods using calcium-release stabilizing immunophilins, junctophilins or calmodulin are also disclosed.

10 Claims, 4 Drawing Sheets

(56) References Cited

OTHER PUBLICATIONS

Skolnick et al. "From genes to protein structure and function: novel applications of computational approaches in the genomic era." Trends Biotechnol. Jan. 2000;18(1):34-9.*
Kang, Cong Bao, et al.: "FKBP Family Proteins: Immunophilins with Versatile Biological Functions", Neurosignals, Jul. 18, 2008, vol. 16, pp. 318-325.
Galet, Andrzej: "Functional diversity and pharmacological profiles of the FKBPs and their complexes with small natural ligands", Cellular and Molecular Life Sciences, 2013, vol. 70, pp. 3243-3275.
Gandy, Sam: "Alzheimer's Disease: New Data Highlight Non-neuronal Cell Types and the Necessity for Presymptomatic Prevention Strategies", Biol Psychiatry 2013, Published by Elsevier Inc.
Michael J. Berridge, "Dysregulation of neural calcium signaling in Alzheimer disease, bipolar disorder and schizophrenia". Landes Bioscience. vol. 7, Iss. 1. Jan.-Feb. 2013.
Marie K. Bosch et al. "Dual Transgene Expression in Murine Cerebellar Purkinje Neurons by Viral Transduction In Vivo". PLOS One 9(8). Aug. 2014.
Boris Kantor et al. "Methods for Gene Transfer to the Central Nervous System" Adv Genet. 2014; 87: 125-197.
Christopher H. George et al., "Developing New Anti-Arrhythmics: Clues from the Molecular Basis of Cardiac Ryanodine Receptor (RyR2) $Ca^{2+}$—Release Channel Dysfunction", Current Pharmaceutical Design, 2007, 13, pp. 3195-3211.
Steven J. Gray et al., "Viral Vectors and Delivery Strategies for CNS Gene Therapy", Ther Deliv. Oct. 2010, 1(4), pp. 517-534.
Boris Kantor et al., "Clinical Applications Involving CNS Gene Transfer", Adv. Genet. 2014:87, pp. 71-124.
Christophe Morisseau et al., "Toxicology in the Fast Lane: Application of High-Throughput Bioassays to Detect Modulation of Key Enzymes and Receptors", Environmental Health Perspectives, vol. 117, No. 12, Dec. 2009, pp. 1867-1872.
Dr. Agostina Puppo et al., "Retinal transduction profiles by high-capacity viral vectors", Gene Ther., Oct. 2014, 21(10) pp. 855-865.
Shilpa Ramaswamy et al., "Gene therapy for Huntington's disease", Neurobiology of Disease, 48(2012) pp. 243-254.
Eun Hui Lee et al. "N-terminal Reigon of FKBP12 Is Essential for Binding to the Skeletal Ryanodine Receptor". The Journal of Biological Chemistry vol. 279, No. 25. Jun. 18, 2004. pp. 26481-26488.
Hong-Bo Xin et al. "Three Amino Acid Residues Determine Selective Binding of FK506-binding Protein 12.6 to the Cardiac Ryanodine Receptor". The Journal of Biological Chemistry. vol. 274. No. 22. May 28, 1999. pp. 15315-15319.
Mihail G. Chelu et al. "Regulation of Ryanodine Receptors by FK506 Binding Proteins" Trends In Cardiovascular Medicine. vol. 14. No. 6. Aug. 2004. pp. 227-234.

* cited by examiner

METHODS FOR DIAGNOSING AND TREATING ALZHEIMER'S DISEASE (AD) USING THE MOLECULES THAT STABILIZE INTRACELLULAR CALCIUM ($CA_{2+}$) RELEASE

RELATED APPLICATIONS

This application claims priority to U.S. Provisional Patent Application No. 61/533,056, filed Sep. 9, 2011, the entire content of which is hereby incorporated herein by reference as though fully set forth here.

GOVERNMENT LICENSE RIGHTS

The subject technology was made with government support under grants AG034605, AG004542 and AG010836 awarded by National Institute on Aging. The Government may have certain rights to this invention.

SEQUENCE LISTING

The instant application contains a Sequence Listing which has been submitted in ASCII format via EFS-Web and is hereby incorporated by reference in its entirety. Said ASCII copy, created on Dec. 27, 2012, is named Sequence Listing 50229-0611.txt and is 1,121 bytes in size.

FIELD

The subject technology relates to methods and compositions for treating Alzheimer's disease (AD) or other cognitive disorders; it also relates to a method of diagnosing individuals who are at risk of developing AD. More specifically, the subject technology relates to calcium release-stabilizing molecules that can reduce, inhibit or reverse calcium dysregulation in brain cells.

BACKGROUND

The characteristic neuropathological and molecular lesions that correlate with dementia in Alzheimer's Disease (AD) include the accumulation of hyper-phosphorylated and poly-ubiquinated microtubule-associated proteins, such as tau, resulting in the formation of neurofibrillary tangles, dystrophic neuritis, and neuropil threads. Neuronal cytoskeletal abnormalities are associated with cerebral atrophy with cell and fiber loss, and synaptic disconnection. Increased amyloid-beta (Aβ) deposition around and within the walls of meningeal and cortical vessels, the cortical neuropil, and neuronal perikarya is a feature of both AD and normal aging. Although genetic factors can predispose individuals to develop premature and excessive cerebral deposits of Aβ in AD-type dementia, most cases are sporadic and do not exhibit clear familial or genetic clustering. Recent exploration of biochemical, molecular, and cellular abnormalities that precede or accompany classic AD demonstrated that cell loss was associated with increased activation of pro-death genes and signaling pathways, impaired energy metabolism, mitochondrial dysfunction, chronic oxidative stress, and cerebrovascular disease/cerebral hypoperfusion. However, the inability to interlink these phenomena under a single primary pathogenic mechanism resulted in the emergence and propagation of various heavily debated theories, each of which focused on how one particular component of AD could trigger a cascade that contributes to the development of all other known abnormalities.

Currently, the major pathological factors known to be involved in Alzheimer's Disease (AD) include beta amyloid accumulation, neurofibrillary tangles (NFTs) and synaptic dysfunction or loss. In addition, AD is associated with other pathological processes, including failing mitochondrial function and oxidative stress, increased inflammatory response, protein misfolding, altered growth factor signaling, aberrant reentry of neurons into the cell cycle, lysosomal activation, endocrine alteration, insulin resistance, cholesterol dyshomeostasis, and calcium dysregulation.

The complexity and number of changes associated with AD has impeded attempts to disentangle the processes important for pathogenesis and discover a treatment of AD. Therefore, there sill remains a need for identifying agents or molecules that can be used for diagnosis and/or treating AD.

SUMMARY

The subject technology is illustrated, for example, according to various aspects described below.

In some embodiments, the subject technology relates to a method of treating Alzheimer's Disease (AD), early-stage AD, elevated risk of AD, mild cognitive impairment (MCI), or other forms of age-related cognitive decline in a subject in need thereof. This method includes administering to the subject a molecule or combination of molecules that promote calcium-release stabilization in ryanodine receptors (RyR) and/or inositol triphosphate receptors (InsP3R) in the brain cells of the subject. In certain embodiments, the molecule is a polypeptide, polynucleotide, small molecule or large molecule. In an embodiment, the molecule is a polypeptide selected from immunophilins, junctophilins or calmodulins. In another embodiment, the polypeptide molecule is FKBP1a, FKBP1b, junctophilin 3, junctophilin 4, calmodulin 3, a functional fragment thereof or combinations thereof. In another embodiment, the molecule is a polynucleotide encoding a polypeptide selected from immunophilins, junctophilins or calmodulins. In another embodiment, the polynucleotide molecule is a nucleic acid sequence encoding at least one of FKBP1a, FKBP1b, junctophilin 3, junctophilin 4, calmodulin 3, a functional fragment thereof or combinations thereof. In some embodiments, the molecule is administered orally, ophthalmically, nasally, urogentially, rectally, dermally, or by way of injection/infusion into tissue or blood.

In some embodiments, the subject technology relates to a method of treating Alzheimer's Disease (AD), early-stage AD, elevated risk of AD, mild cognitive impairment (MCI), or other forms of age-related cognitive decline (collectively cognitive decline) in a subject in need thereof. This method includes administering to the subject a calcium (Ca2+)-release stabilizing molecule, wherein said molecule induces reduction, inhibition or reversal of Ca2+ dysregulation in brain cells of the subject thereby stabilizing or reducing the cognitive decline. In certain embodiments, the molecule is a polypeptide, polynucleotide, small molecule or large molecule. In an embodiment, the molecule is a polypeptide selected from immunophilins, junctophilins or calmodulins. In another embodiment, the polypeptide molecule is FKBP1a, FKBP1b, junctophilin 3, junctophilin 4, calmodulin 3, a functional fragment thereof or combinations thereof. In another embodiment, the molecule is a polynucleotide encoding a polypeptide selected from immunophilins, junctophilins or calmodulins. In another embodiment, the polynucleotide molecule is a nucleic acid sequence encoding at least one of FKBP1a, FKBP1b, junctophilin 3, junctophilin 4, calmodulin 3, a functional fragment thereof or combinations thereof. In some embodiments, the molecule is administered orally, ophthalmically, nasally, urogentially, rectally, dermally, or by way of injection/infusion into tissue or blood.

In some embodiments, the subject technology relates to a method for diagnosing Alzheimer's Disease (AD), early-stage AD, elevated risk of AD or mild cognitive impairment (MCI) in a patient. This method includes (1) obtaining a biological sample from the patient, (2) detecting the level of expression of one or more calcium-release stabilizing immunophilin, junctophilin and/or calmodulin genes in the biological sample from said patient, wherein differential expression of said one or more genes in the sample as compared to control levels of expression of said one or more genes is indicative of Alzheimer's Disease (AD), early-stage AD, elevated risk of AD or mild cognitive impairment (MCI). In an embodiment, the biological sample is blood, muscle tissue, brain tissue, peripheral nervous system, cerebrospinal fluid sample or any tissue sample exhibiting significant concentrations of immunophilins, junctophilins or calmodulin. In another embodiment, the patient exhibits symptoms of Alzheimer's Disease (AD), early-stage AD, elevated risk of AD or mild cognitive impairment (MCI) or is being treated for Alzheimer's Disease (AD) or mild cognitive impairment (MCI). In another embodiment, the level of expression of one or more genes is determined by a nucleic acid polymerization or hybridization technology. In another embodiment, at least one of the genes whose level of expression is being determined includes FKBP1a, FKBP1b, junctophilin 3, junctophilin 4, calmodulin 3 or a variant thereof. In another embodiment, the one or more genes are differentially expressed in one or more brain regions of the patient, said brain regions being selected from the group consisting of hippocampal formation, entorhinal cortex, paleocortex and neocortex. In another embodiment, the level of expression of said one or more genes is normalized to the expression level of a housekeeping gene as a control.

In some embodiments, the subject technology relates to a method for diagnosing Alzheimer's Disease (AD), early-stage AD, elevated risk of AD or mild cognitive impairment (MCI) in a patient. This method includes (1) obtaining a biological sample from the patient, (2) detecting the level of expression of one or more calcium-release stabilizing immunophilin, junctophilin and/or calmodulin genes in the biological sample from said patient, wherein differential expression of said one or more genes in the sample as compared to control levels of expression of housekeeping genes, genes whose expressions are known not to change with AD, or the same genes obtained from normal subjects who do not have AD is indicative of Alzheimer's Disease (AD), early-stage AD, elevated risk of AD or mild cognitive impairment (MCI). In an embodiment, the biological sample is blood, muscle tissue, brain tissue, peripheral nervous system, cerebrospinal fluid sample or any tissue sample exhibiting significant concentrations of immunophilins, junctophilins or calmodulin. In another embodiment, the patient is exhibiting symptoms of Alzheimer's Disease (AD), early-stage AD, elevated risk of AD or mild cognitive impairment (MCI) or is being treated for Alzheimer's Disease (AD) or mild cognitive impairment (MCI). In another embodiment, the level of expression of one or more genes is determined by a nucleic acid polymerization or hybridization technology. In another embodiment, at least one of the genes whose level of expression is being determined includes FKBP1a, FKBP1b, junctophilin 3, junctophilin 4, calmodulin 3 or a variant thereof. In another embodiment, the one or more genes are differentially expressed in one or more brain regions of the patient, said brain regions being selected from the group consisting of hippocampal formation, entorhinal cortex, paleocortex and neocortex. In another embodiment, the level of expression of said one or more genes is compared to the expression level of one or more housekeeping genes. In another embodiment, the level of expression of said one or more genes is compared to the expression level of one or more genes used as control.

Additional features and advantages of the subject technology will be set forth in the description below, and in part will be apparent from the description, or may be learned by practice of the subject technology. The advantages of the subject technology will be realized and attained by the structure particularly pointed out in the written description and claims hereof as well as the appended drawings.

It is to be understood that both the foregoing general description and the following detailed description are exemplary and explanatory and are intended to provide further explanation of the subject technology as claimed.

BRIEF DESCRIPTION OF THE DRAWINGS

The accompanying drawings, which are included to provide further understanding of the subject technology and are incorporated in and constitute a part of this specification, illustrate aspects of the subject technology and together with the description serve to explain the principles of the subject technology.

DETAILED DESCRIPTION

Figure 1:
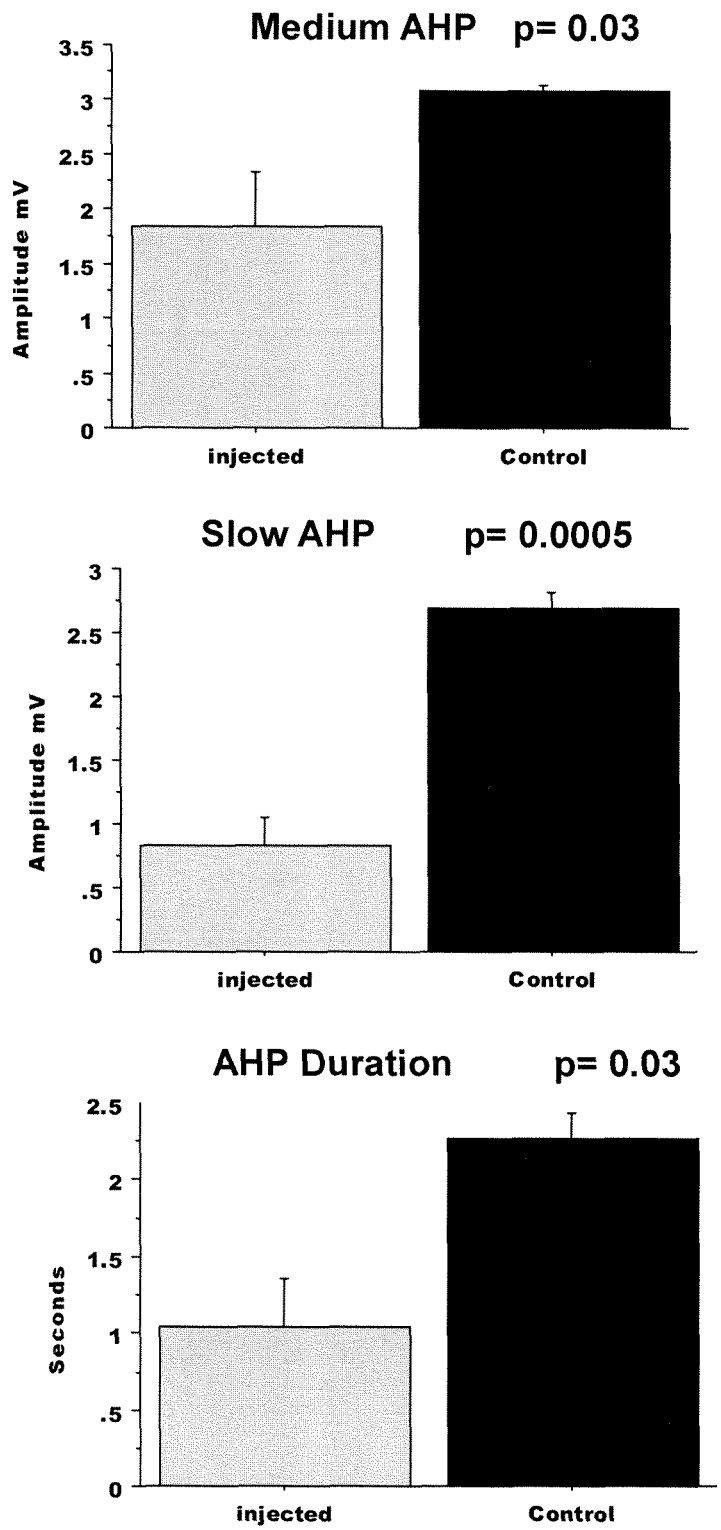
FIG. 1 is a bar chart depicting electrophysiological effects of unilateral microinjection into one hippocampus of aging rats of adeno-associated viral (AAV) vector containing the open reading frame (ORF) of the Fkbp1b gene. This microinjection resulted in overexpression of FKBP1b mRNA and protein (confirmed by qPCR and immunohistochemistry). Shown are the quantitative group measures (mean+/−SEM) of intracellular electrode recordings of membrane voltage responses that are well-established to vary in magnitude with the amount of calcium released by intracellular ryanodine receptors (RyRs); these voltage responses are the amplitude of the calcium-dependent medium afterhyperpolarization (mAHP) (top panel), amplitude of the calcium-dependent slow afterhyperpolarization (sAHP) (middle panel), and duration of the calcium-dependent slow afterhyperpolarization (sAHP) (bottom panel). The data reveal significant differences in these responses in neurons recorded from the viral vector-injected hippocampus vs. those recorded from the control (non-injected) hippocampus, such that the injected-side neurons exhibit a younger phenotype (lesser magnitude). Larger amplitude AHPs develop with aging and have been correlated with impaired memory.
Figure 2:
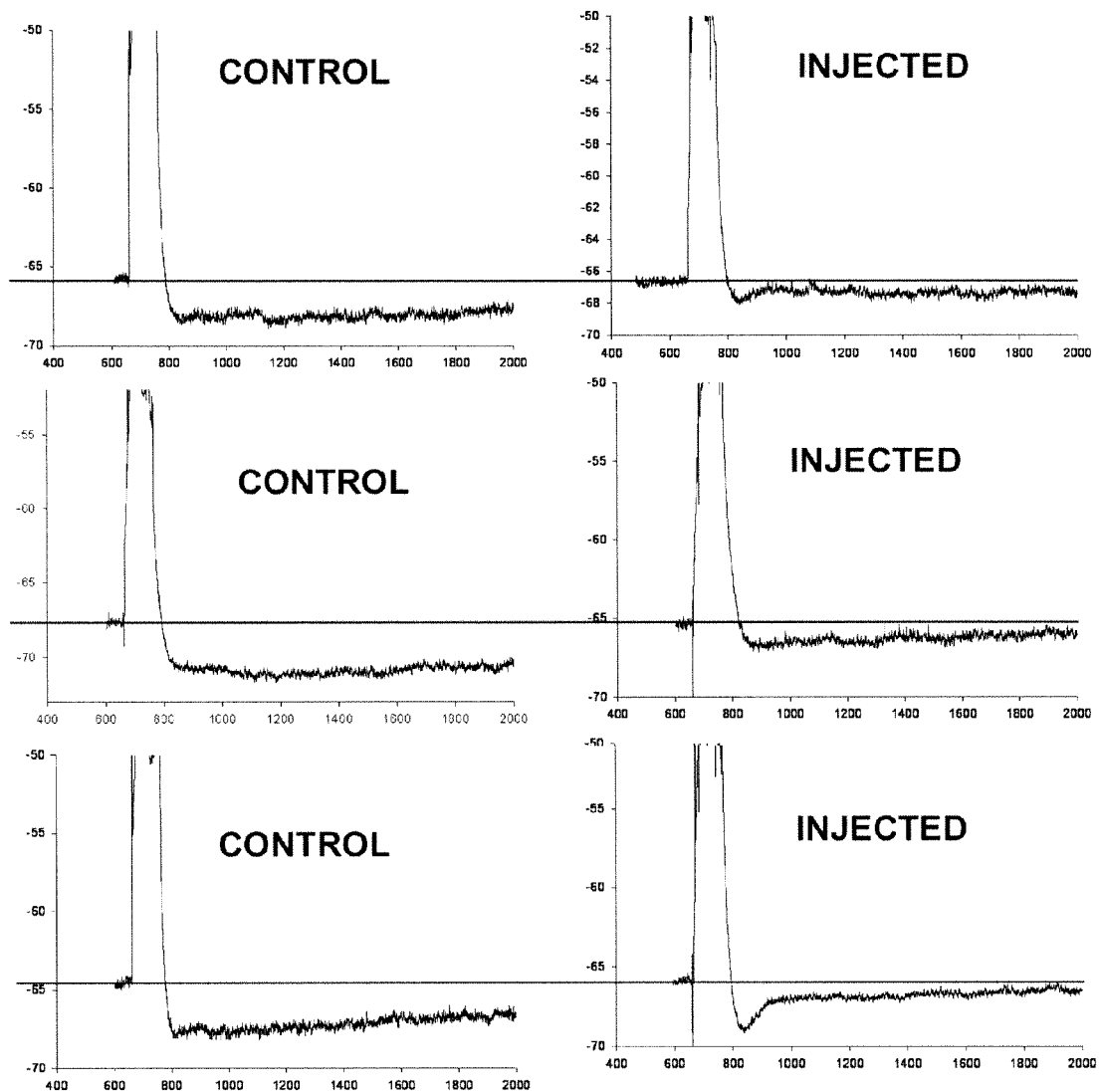
FIG. 2 shows representative examples of the membrane voltage responses (for which the quantitative data are shown in FIG. 1). Left Column: AHPs that follow an induced burst of 4 action potentials (truncated for illustration) in 3 control-side hippocampal neurons. Right Column: AHPs that follow an induced burst of 4 action potentials in 3 injected-side hippocampal neurons. The AHPs are substantially smaller in the injected-side neurons, indicating that the overexpression of FKBP1b has stabilized ryanodine receptors and decreased release of calcium from intracellular storage sites. Y-axis: membrane holding potential (no significant differences between control and injected neurons); X-axis: Time (msec).

In the following detailed description, numerous specific details are set forth to provide a full understanding of the subject technology. It will be apparent, however, to one ordinarily skilled in the art that the subject technology may be practiced without some of these specific details. In other instances, well-known structures and techniques have not been shown in detail so as not to obscure the subject technology.

With aging, multiple $Ca^{2+}$-associated electrophysiological processes exhibit increased magnitude in hippocampal pyramidal neurons, including the $Ca^{2+}$-dependent slow afterhyperpolarization (sAHP), L-type voltage-gated $Ca^{2+}$ channel (L-VGCC) activity, $Ca^{2+}$-induced $Ca^{2+}$ release (CICR) from ryanodine receptors (RyRs), and $Ca^{2+}$ transients. This pattern of $Ca^{2+}$ dysregulation correlates with reduced neuronal excitability/plasticity and impaired learning/memory and has been proposed to contribute to unhealthy brain aging and Alzheimer's disease. However, little is known about the underlying molecular mechanisms.

The inventors have recently found that expression of the Ca2+-stabilizing molecules, FKBP1a, FKBP1b, junctophilin 3, junctophilin 4, and calmodulin 3 decreases in hippocampus of humans with early-stage AD and that this decrease correlates with incipient cognitive dysfunction (Blalock et al., J. Chemical Neuroanatomy 42:118-126; July 2011). They have further observed that disrupting FKBP1b function destabilizes $Ca^{2+}$ homeostasis in hippocampal neurons and is sufficient to induce the aging phenotype of $Ca^{2+}$ dysregulation in young animals. In their study, the inventors found that disruption of FKBP1b recapitulated much of the $Ca^{2+}$-dysregulation aging phenotype in young rat hippocampus, supporting the hypothesis that declining FKBP function plays a major role in unhealthy brain aging (Gant et al., J. Neuroscience, 31 (5): 1693-1703; February 2011).

However, the subject technology relates, in part, to an unexpected discovery that over expression of the Fkbp1b open reading frame (ORF) in the hippocampus of aging rats not only counteracts $Ca^{2+}$ dyshomeostasis, but also improves maze learning and/or memory in rats. This unexpected discovery suggests that Fkpb1b and other $Ca^{2+}$ release-stabilizing molecules including immunophilins such as Fkbp1a, junctophilins such as junctophilins 3 and 4 or clamodulins such as chalmodulin 3, as well as intraneuronal calcium channels such as ryanodine receptors (RyRs) and/or Inositol trisphosphate receptor (InsP3R) are novel therapeutic molecules and/or targets for interventions aimed at protection against unhealthy brain aging or Alzheimer's disease through stabilization of $Ca^{2+}$ release mechanisms in brain cells.

Accordingly, in some embodiments, the subject technology relates to a method of treating Alzheimer's Disease (AD), early-stage AD, elevated risk of AD, mild cognitive impairment (MCI), or other forms of age-related cognitive decline in a subject in need thereof, by administering to the subject a molecule that promotes calcium-release stabilization in ryanodine receptors (RyR) and/or inosital triphosphate receptors (InsP3R) in brain cells.

In some embodiments, the subject technology relates to a method of treating Alzheimer's Disease (AD), early-stage AD, elevated risk of AD, mild cognitive impairment (MCI), or other forms of age-related cognitive decline in a subject in need thereof, comprising administering to the subject a calcium ($Ca^{2+}$)-release stabilizing molecule, wherein said molecule induces reduction, inhibition or reversal of $Ca^{2+}$ dysregulation in brain cells of the subject.

In some embodiments, the therapeutic molecule of the subject technology includes a polypeptide, polynucleotide, small molecule or large molecule. The polypeptide suitable for use in this embodiment can be selected from immunophilins, junctophilins or calmodulins. More specifically, the polypeptide is a full-length amino acid sequence of at least one FKBP1a, FKBP1b, junctophilin 3, junctophilin 4, calmodulin 3 or a functional fragment thereof. The polynucleotide suitable for use in this embodiment can be polynucleotide encoding a polypeptide selected from immunophilins, junctophilins or calmodulins. More specifically, the polynucleotide is a nucleic acid sequence encoding at least one of FKBP1a, FKBP1b, junctophilin 3, junctophilin 4, calmodulin 3 or a functional fragment thereof. In another related embodiment, the molecule is administered orally, ophthalmically, nasally, urogentially, rectally, dermally, or by way of injection/infusion into tissue or blood.

In some embodiments, the subject technology relates to a method of diagnosing Alzheimer's Disease (AD), early-stage AD, elevated risk of AD or mild cognitive impairment (MCI) in a patient, including: detecting the level of expression of one or more calcium-release stabilizing immunophilin, junctophilin and/or calmodulin genes in a biological sample from said patient, wherein differential expression of said one or more genes in the sample as compared to control levels of expression of said one or more genes, or to levels of expression in the same patient of other control genes known not to change with AD, is indicative of Alzheimer's Disease (AD), early-stage AD, elevated risk of AD or mild cognitive impairment (MCI).

Definitions:

To facilitate an understanding of the present subject technology, a number of terms and phrases are defined below:

As used herein, the term "early-stage AD" refers to incipient Alzheimer's Disease characterized by at least some of and in many cases all of the following signs and symptoms: recent memory is impaired; learning and retaining new information becomes difficult. Language problems (especially with word finding), mood swings, and personality changes develop. Patient may have progressive difficulty with independent activities of daily living (e.g., balancing their checkbook, finding their way around, remembering where they put things). Abstract thinking, insight, or judgment may be impaired. Patients may respond to loss of independence and memory with irritability, hostility, and agitation. Functional ability may be further limited by the following: Agnosia: Impaired ability to identify objects despite intact sensory function; Apraxia: Impaired ability to do previously learned motor activities despite intact motor function; and Aphasia: Impaired ability to comprehend or use language. Although early-stage AD may not compromise sociability, family members may report strange behavior accompanied by emotional lability. Pathophysiologically, early-stage AD refers to the beginning stages of amyloid β(A β)-protein deposit in the brain. Additional information related to identifying early-stage AD are provided by the American Academy of Neurology (AAN). Early stage AD can further be described in terms of the Mini Mental State Examination (MMSE) score (See Blalock et al., PNAS 101(7):2173-2178 (2004)). For example, subjects can be categorized into the following four groups based on MMSE score: "Control" (MMSE>25), "Incipient AD" (MMSE=20-26), "Moderate AD" (MMSE=14-19), and "SevereAD" (MMSE<14). Earlystage AD can further be described as a stage prior to onset of intermediate- or late-stage AD.

In intermediate stage AD, patients are unable to learn or recall new information. Memory of remote events is reduced, but not totally lost. Patients may require help with basic activities of daily living (e.g., bathing, eating, dressing, toileting). Personality changes may progress. Patients may become irritable, anxious, self-centered, inflexible, or angry more easily, or they may become more passive, with a flat affect, depression, indecisiveness, lack of spontaneity, or general withdrawal from social situations. Behavior disorders may develop: Patients may wander or become suddenly and inappropriately agitated, hostile, uncooperative, or physically aggressive. By this stage, patients have lost all sense of time and place because they cannot effectively use normal environmental and social cues. Patients often get lost; they may be unable to find their own bedroom or bathroom. They remain ambulatory but are at risk of falls or accidents secondary to confusion. Altered sensation or perception may culminate in psychosis with hallucinations and paranoid and persecutory delusions. Sleep patterns are often disorganized.

In late or severe stage of AD, patients cannot walk, feed themselves, or do any other activities of daily living; they may become incontinent. Recent and remote memory is completely lost. Patients may be unable to swallow. They are at risk of malnutrition, pneumonia (especially due to aspiration), and pressure ulcers. Because they depend completely on others for care, placement in a long-term care facility often becomes necessary. Eventually, patients become mute.

As used herein, the term "mild cognitive impairment (MCI)" takes its ordinary meaning in the art. MCI mostly refers to a condition that is more severe than age-associated memory impairment. In MCI, memory is impaired compared with that of age-matched controls, but other cognitive domains and daily function are not affected. Up to 50% of patients with mild cognitive impairment develop dementia within 3 yr. Normally, patients with MCI once identified are monitored for progression to AD. MCI is an intermediate stage between the expected cognitive decline of normal aging and the more serious decline of dementia. It can involve problems with memory, language, thinking and judgment that are greater than normal age-related changes. Patients with mild cognitive impairment may be aware that their memory or mental function has "slipped." Their families and close friends also may notice a change. But generally these changes aren't severe enough to interfere with the patients' day-to-day life and usual activities.

As used herein, the term "elevated risk of AD" refers to situations where a patient suffers from MCI or shows one or more of the 10 warning signs of AD (according to the American Academy of Neurology guidelines on dementia, and the Alzheimer's Association. These 10 warning signs are: 1. Memory loss that affects job skills; 2. Difficulty performing familiar tasks; 3. Problems with language; 4. Disorientation to time and place; 5. Poor or decreased judgment; 6. Problems with abstract thinking; 7. Misplacing things; 8. Changes in mood or behavior; 9. Changes in personality; 10. Loss of initiative. Also, it is known that there is a familial pattern of AD, thus first-degree biological relatives of individuals with AD may be at an elevated risk of AD than the general population.

As used herein, a "subject" is preferably a mammal and more preferably a human, but can be any animal, including a laboratory animal in the context of a clinical trial or screening or activity experiment. Thus, as can be readily appreciated by one of ordinary skill in the art, the methods of the subject technology are particularly suited to administration to any animal, particularly a mammal, and including, but not limited to domestic animals, wild animals and research animals.

As used herein, the term "inhibit" means preventing or delaying the onset or progression of one or more clinical symptoms of AD. Common early symptoms of Alzheimer's include confusion, disturbances in short-term memory, problems with attention and spatial orientation, personality changes, language difficulties, unexplained mood swings.

The term "therapeutically effective amount" is used herein to mean an amount or dose of a molecule of the subject technology that is effective to ameliorate, delay, or prevent any of the foregoing symptoms, behaviors or events associated with Alzheimer's disease or related neurodegenerative disorders including MCI. Alternatively, a therapeutically effective amount is sufficient to cause an improvement in a clinically significant condition in the individual.

As used herein, the phrase "pharmaceutically acceptable" refers to molecular entities and compositions that are "generally regarded as "safe," e.g., that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government of listed in the U.S. Pharmacopeia or other generally recognized pharmacopeia for use in animals, and more particularly in humans.

The term "treat" is used herein to mean to relieve or alleviate at least one symptom of a disease in a subject. As used herein, the term "treat" also denotes to arrest, delay the onset (i.e., the period prior to clinical manifestation of a disease) and/or reduce the risk of developing or worsening a disease.

The term "promote" as used herein means to have any positive effect or benefit. As used, the term is relative and does not necessarily mean to enhance or improve. For example, a molecule of the subject technology that stabilizes calcium release (as measured electrophysiologically) in ryanodine receptors (RyR) and/or inositol triphosphate receptors (InsP3R) of neurons and/or muscle cells by at least 5% as compared to control cells not receiving such molecule could still be deemed as having a promoting effect.

The terms "reference" or "control" as used herein in relation to an expression profile refers to a normalized pattern of gene or gene product expression or levels of expression of certain biomarkers to be used to compare the level of expression of the targets (e.g., FKBP1a, FKBP1b, junctophilin 3, junctophilin 4, calmodulin 3 or a variant thereof) of the subject technology to for the purpose of interpreting the expression data obtained from a patient and assigning the patient a prognostic or predictive class such as, for example, no AD, at risk of AD, elevated risk of AD or AD. These biomarkers can be housekeeping genes or proteins whose expressions remain unaffected by AD or clinical symptoms of AD or MCI. The biomarkers can also be those obtained from one or more healthy individuals known not to have AD or clinical symptoms of AD. The biomarkers can also be those obtained from a universal control sample obtained by pooling a statistically significant number of mRNAs or cDNAs from biological samples (e.g., hippocampal cells or tissues) of healthy individuals known to not have clinical symptoms of AD or MCI.

The terms "about" and "approximately" shall generally mean an acceptable degree of error or variation for the quantity measured given the nature or precision of the measurements. Typical, exemplary degrees of error or variation are within 20 percent (%), preferably within 10%, and more preferably within 5% of a given value or range of values. For biological systems, the term "about" refers to an acceptable standard deviation of error, preferably not more than 2-fold of a give value. Numerical quantities given herein are approximate unless stated otherwise, meaning that the term "about" or "approximately" can be inferred when not expressly stated.

The term "differential expression" refers to both quantitative as well as qualitative differences in the temporal and tissue expression patterns of a gene. For example, a differentially expressed gene may have its expression activated or completely inactivated in normal versus disease conditions. Such a qualitatively regulated gene may exhibit an expression pattern within a given tissue or cell type that is detectable in either control or disease conditions, but is not detectable in both.

The term "polypeptide" includes a compound of two or more subunit amino acids, amino acid analogs, or peptidomimetics. The subunits may be linked by peptide bonds. In another embodiment, the subunit may be linked by other bonds, e.g., ester, ether, etc. As used herein the term "amino acid" includes either natural and/or unnatural or synthetic amino acids, including glycine and both the D or L optical isomers, and amino acid analogs and peptidomimetics. A peptide of three or more amino acids is commonly referred to as an oligopeptide. Peptide chains of greater than three or more amino acids are referred to as a polypeptide or a protein.

"Hybridization" includes a reaction in which one or more polynucleotides react to form a complex that is stabilized via hydrogen bonding between the bases of the nucleotide residues. The hydrogen bonding may occur by Watson-Crick base pairing, Hoogstein binding, or in any other sequence-specific manner. The complex may comprise two strands forming a duplex structure, three or more strands forming a multi-stranded complex, a single self-hybridizing strand, or any combination of these. A hybridization reaction may constitute a step in a more extensive process, such as the initiation of a PCR reaction, or the enzymatic cleavage of a polynucleotide by a ribozyme.

Hybridization reactions can be performed under conditions of different "stringency". The stringency of a hybridization reaction includes the difficulty with which any two nucleic acid molecules will hybridize to one another. Under stringent conditions, nucleic acid molecules sharing at least 60%, 65%, 70%, 75% identity to each other (throughout the entire sequence) remain hybridized to each other, whereas molecules with low percent identity cannot remain hybridized. A preferred, non-limiting example of highly stringent hybridization conditions are hybridization in 6× sodium chloride/sodium citrate (SSC) at about 45° C., followed by one or more washes in 0.2×SSC, 0.1% SDS at 50° C., preferably at 55° C., more preferably at 60° C., and even more preferably at 65° C.

As used herein the term "target" refers to the polypeptides and polynucleotides of the subject technology including immunophilins, junctophilins, calmodulins (whose function is to stabilize calcium release from calcium channels RyR and InsP3R), ryanodine receptors (RyRs) and inositol triphosphate receptors (InsP3Rs). Exemplary immunophilins, junctophilins or calmodulins are Fkbp1a; Fkbp1b variant (a); Fkbp1b variant (b); Junctophilin 3; Junctophilin 4, Calmodulin 3. The modulation of quantity or activity of the target can result in inhibition, prevention, amelioration, treatment or reduction in the aging phenotype of $Ca^{2+}$ dysregulation in a subject with AD, MCI or other cognitive impairments. The cDNA and protein sequences of the exemplary targets of the subject technology can be obtained from the National Center for Biotechnology Information (NCBI) databases using the accession numbers listed in table below.

| Name | cDNA Accession No. | Protein Accession No. |
|---|---|---|
| Fkbp1a | cDNA: NM_000801.4 | Protein: NP_000792.1 |
| Fkbp1b variant_a | cDNA: NM_004116.3 | Protein: NP_004107.1 |
| Fkbp1b variant_b | cDNA: NM_054033.2 | Protein: NP_473374.1 |
| Junctophilin 3 | cDNA: NM_020655.2 | Protein: NP_065706.2 |
| Junctophilin 4 | cDNA: NM_001146028.1 | Protein: NP_001139500.1 |
| Calmodulin 3 | cDNA: NM_005184.2 | Protein: NP_005175.2 |

As used herein, the term "panel of targets" includes a group of targets, the quantity or activity of each member of which is correlated with the incidence or risk of incidence of AD or other cognitive impairments. In certain embodiments, a panel of targets may include only those targets which are either increased or decreased in quantity or activity in subjects afflicted with or cells involved in AD or other cognitive impairments. In other embodiments, a panel of targets may include only those targets present in a specific tissue type which are correlated with the incidence or risk of incidence of AD or other cognitive impairments.

As used herein, the term "small molecule" refers to a non-peptidic, non-oligomeric organic compound either synthesized in the laboratory or found in nature. Small molecules, as used herein, can refer to compounds that are "natural product-like", however, the term "small molecule" is not limited to "natural product-like" compounds. Rather, a small molecule is typically characterized in that it contains several carbon-carbon bonds, and has a molecular weight of less than 2000 g/mol, preferably less than 1500 g/mol, although this characterization is not intended to be limiting for the purposes of the subject technology. Small molecules are typically characterized by multiple carbon-carbon bonds and may have one or more stereocenters. Examples of "small molecules" that occur in nature include, but are not limited to, taxol, dynemicin, rapamycin or JTV519 (K201). Examples of "small molecules" that are synthesized in the laboratory include, but are not limited to, compounds described by Tan et al. ("Stereoselective Synthesis of over Two Million Compounds Having Structural Features Both Reminiscent of Natural Products and Compatible with Miniaturized Cell-Based Assays" J. Am. Chem. Soc. 120:8565, 1998; incorporated herein by reference). In certain other preferred embodiments, natural-product-like small molecules are utilized. In certain embodiments, the small molecule is not polymeric or oligomeric. In certain embodiments, the small molecule is not a nucleic acid, protein, or peptide.

As used herein, the term large molecule refers to a drug having a molecular weight higher than about 2000 g/mol. Exemplary large molecules include synthetic polymers or macromolecules with equal to or grater 2000 g/mol of molecular weight. In certain embodiments, the large molecule is not a nucleic acid, protein, or peptide.

Previously, it was established that several classes of molecules, including immunophilins, junctophilins, and calmodulin 3 (CALM3) play a necessary role in stabilizing $Ca^{2+}$ release from intracellular stores such as RyRs in muscle and cardiac cells.

In previous studies conducted in the inventors' lab, it was shown that the expression of the FKBP1b gene, which encodes the FK-506 binding protein 1b (FKBP1b, aka FKBP12.6), is decreased in hippocampal cells of patients with early-stage AD (Blalock et al., Proc. Natl. Acad. Sci. U.S.A. 101:2173-2178 (2004)) and in aging rats (Kadish et al., J. Neurosci., 29:1805-1816 (2009)). Because the study was conducted on hand-dissected frozen hippocampal CA1 blocks containing both white and gray matter, the authors found that it was not possible to distinguish transcriptional changes. Further, since heterogeneous cells types/regions were mixed together in these studies, tissue-specific changes were obscured. No definitive conclusion on the role of FKBP1b in cognition and AD could be drawn or suggested.

In a more recent study (Blalock et al, 2011), a gene expression profiling of the laser-captured gray matter regions of hippocampal sections revealed that, with AD, brain (hippocampal) expression also decreases for a plurality of genes that encode proteins that stabilize $Ca^{2+}$ release from RyRs in muscle cells, including FKBP1b, FKBP1a, two junctophilins and CALM3. Further, it was found that the decreased expression of these molecules correlated with decreased cognitive function in early-stage AD patients.

In another more recent study (Gant et al., 2011), it was shown that directly manipulating FKBP1b in key brain regions of rats, by microinjecting an inactivated viral vector containing short interfering RNA against Fkbp1b, can induce $Ca^{2+}$ dysregulation (measured electrophysiologically) related to memory loss and aging phenotype.

Although the inventors' recent studies established a link between the down-regulation or disruption of genes that encode $Ca^{2+}$ release-stabilizing molecules and the $Ca^{2+}$ dysregulation or decreased cognitive function in early-stage AD patients, it was unexpected to discover, as shown herein, that microinjection of viral vector bearing the open reading frame (orf) of one of the above genes, i.e., the FKBP1b gene, into the hippocampus of rats results in overexpression of FKBP1b in regions critical for memory (hippocampus) and stabilizes $Ca^{2+}$ release. It was even more unexpected to discover that this reversal of $Ca^{2+}$ dysregulation resulted in an improved memory. Thus, according to the subject technology, the stabilization of $Ca^{2+}$ release from the calcium receptors such as RyRs or InsP3R, as observed in the present disclosure, leads to the reversal of $Ca^{2+}$ dysregulation and indicates that both the receptors and molecules that stabilize these receptors can be used as targets for developing diagnostic and/or therapeutic means for treating or inhibiting memory loss, AD, MCI, and other cognitive or memory impairments.

Ryanodine receptors (RyRs) form a class of intracellular calcium channels in various forms of excitable animal tissue like muscles and neurons. It is the major cellular mediator of calcium-induced calcium release (CICR) in animal cells. There are multiple isoforms of ryanodine receptors including: RyR1 (Entrez ID No. 6261; Hugo ID. No. 10483; Omim ID. No. 180901; RefSeq ID No. NM_000540; and UniProt ID No. P21817); RyR2 (Entrez ID No. 6262; Hugo ID. No. 10484; Omim ID. No. 180902; RefSeq ID No. NM_001035; and UniProt ID No. Q92736); and RyR3 (Entrez ID No. 6263; Hugo ID. No. 10485; Omim ID. No. 180903; RefSeq ID No. NM_001036; and UniProt ID No. Q15413) which is expressed more widely, but especially in the brain.

Inositol trisphosphate receptor (InsP3R) is a membrane glycoprotein complex acting as $Ca^{2+}$ channel activated by inositol trisphosphate (InsP3). InsP3R is very diverse among organisms, and is necessary for the control of cellular and physiological processes including cell division, cell proliferation, apoptosis, fertilization, development, behavior, learning and memory. Inositol triphosphate receptor represents a dominant second messenger leading to the release of $Ca^{2+}$ from intracellular store sites. There is evidence suggesting that InsP3R plays an important role in the conversion of external stimuli to intracellular $Ca^{2+}$ signals characterized by complex patterns relative to both space and time, for example, $Ca^{2+}$ waves and oscillations. The InsP3 receptor was first purified from rat cerebellum. There are multiple isoforms of ryanodine receptors including: InsP3R1 (also abbreviated as ITPR1; Entrez ID No. 3708; Hugo ID. No. 6180; Omim ID. No. 147265; RefSeq ID No. NM_002222; and UniProt ID No. Q14643); InsP3R2 (also abbreviated as ITPR2; Entrez ID No. 3709; Omim ID. No. 600144; RefSeq ID No. NM_002223; and UniProt ID No. Q14571); and InsP3R3 (also abbreviated as ITPR3; Entrez ID No. 3710; Hugo ID. No. 6182; Omim ID. No. 147267; RefSeq ID No. NM_002224; and UniProt ID No. Q14573).

In one embodiment, the subject technology provides a method for diagnosing AD, early-stage AD, mild cognitive impairment (MCI) or elevated risk of AD, comprising taking a biopsy sample from muscle tissue or any other tissue exhibiting significant concentrations of immunophilins, junctophilins or calmodulin3, measuring in that sample RNA expression (content, e.g., by qPCR, microarrays or newer methods) for a plurality of genes that encode $Ca^{2+}$ release-stabilizing molecules (those noted above), also measuring in the same sample RNA content for a number of genes that do not change in brain or muscle with AD, and comparing the ratio of expression of $Ca^{2+}$ release-stabilizing genes to expression of AD-insensitive genes, relative to a normalizing/scaling factor (e.g., average signal of all genes) in the same sample. Alternatively, the ratio of $Ca^{2+}$ stabilizing genes could be compared to values for those same $Ca^{2+}$ stabilizing genes in normal subjects, which would be obtained by averaging across a statistically significant number of control subjects that did not exhibit AD or cognitive decline. Several statistical techniques well-known in the field will allow determination of the degree of deviation of the expression of $Ca^{2+}$ release-stabilizing genes from expression of AD-insensitive genes relative to a normalizing baseline, or from averages of $Ca^{2+}$ release-stabilizing genes in non-AD subjects, thereby providing a quantitative index of deviation that can be used to estimate AD risk or progression. With clinical experience, estimates based on this index will be further validated and become increasingly precise.

In another embodiment, the subject technology relates to a method for treating AD, early-stage AD, mild cognitive impairment (MCI), other forms of aging-related cognitive decline or elevated risk of AD, comprising enhancing activity of one or more $Ca^{2+}$ release-stabilizing molecules in a subject diagnosed with one of the above conditions by injecting the subject in the hippocampus and/or other affected brain regions with a quantity of inactivated virus that has been molecularly engineered to overexpress one or a plurality of genes encoding $Ca^{2+}$ release-stabilizing molecules, as mentioned above, and assessing the treated subject over time for improved performance on cognitive/neuropsychological tests. Alternative embodiments of this subject technology include other delivery methods (eg, non-viral-mediated cellular uptake, microinfusions, targeted pharmacological delivery, etc.) of nucleotide sequences that will increase expression of $Ca^{2+}$-stabilizing molecules in cells in brain regions affected by AD. Other alternative embodiments include methods that do not rely on gene expression, but which enhance activity of $Ca^{2+}$ release-stabilizing molecules through post-translational modifications, microRNAs or pharmacological targeting of $Ca^{2+}$ release-stabilizing molecules or their inhibitors.

Various aspects of the subject technology are described in further detail in the following subsections:

I. Isolated Nucleic Acid Molecules Encoding $Ca^{2+}$ Release-Stabilizing Molecules One aspect of the subject technology pertains to isolated nucleic acid molecules that either themselves are the genetic targets (e.g., variants of any of the $Ca^{2+}$ release-stabilizing molecules disclosed herein) of the subject technology, or which encode the polypeptide targets of the subject technology, or functional fragments thereof. Another aspect of the subject technology relates to using the nucleic acid sequences of Fkbp1a, Fkbp1b variant_a, Fkbp1b variant_b, Junctophilin 3, Junctophilin 4 and Calmodulin 3 to obtain variant molecules encoding proteins that have similar activity, i.e., calcium release-stabilizing activity for ryanodine receptors (RyRs), inosital triphosphate receptors (InsP3Rs). Another aspect of the subject technology pertains to isolated nucleic acid fragments sufficient for use as hybridization probes to identify the nucleic acid molecules encoding the targets of the subject technology in a sample, as well as nucleotide fragments for use as PCR primers for the amplification or mutation of the nucleic acid molecules which encode the targets of the subject technology. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

A nucleic acid molecule of the subject technology, e.g., a variant of FKBP1b, can be isolated using standard molecular biology techniques and the sequence information provided herein. Using all or portion of the nucleic acid sequence of the FKBP gene, e.g., the FKBP1b as a hybridization probe, a target gene of the subject technology or a nucleic acid molecule encoding a polypeptide target of the subject technology can be isolated using standard hybridization and cloning techniques (e.g., as described in Sambrook, J., Fritsh, E. F., and Maniatis, T. Molecular Cloning: A Laboratory Manual. 2nd, ed., Cold Spring Harbor Laboratory, Cold Spring Harbor Laboratory Press, Cold Spring Harbor, N.Y., 1989).

A nucleic acid of the subject technology can be amplified using cDNA, mRNA or alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to target nucleotide sequences, or nucleotide sequences encoding a target of the subject technology can be prepared by standard synthetic techniques, e.g., using an automated DNA synthesizer.

In another embodiment, an isolated nucleic acid molecule of the subject technology comprises a nucleic acid molecule which is a complement of the nucleotide sequence of a target of the subject technology or a portion of any of these nucleotide sequences. A nucleic acid molecule which is complementary to such a nucleotide sequence is one which is sufficiently complementary to the nucleotide sequence such that it can hybridize to the nucleotide sequence, thereby forming a stable duplex.

The nucleic acid molecule of the subject technology, moreover, can comprise only a portion of the nucleic acid sequence of a target nucleic acid of the subject technology, or a gene encoding a target polypeptide of the subject technology, for example, a fragment which can be used as a probe or primer. The probe/primer typically comprises substantially purified oligonucleotide. The oligonucleotide typically comprises a region of nucleotide sequence that hybridizes under stringent conditions to at least about 7 or 15, preferably about 20 or 25, more preferably about 50, 75, 100, 125, 150, 175, 200, 225, 250, 275, 300, 325, 350, 400 or more consecutive nucleotides of a target nucleic acid, or a nucleic acid encoding a target polypeptide of the subject technology.

Probes based on the nucleotide sequence of a target gene or of a nucleic acid molecule encoding a target polypeptide of the subject technology can be used to detect transcripts or genomic sequences corresponding to the target gene(s) and/or target polypeptide(s) of the subject technology. In preferred embodiments, the probe comprises a label group attached thereto, e.g., the label group can be a radioisotope, a fluorescent compound, an enzyme, or an enzyme co-factor. Such probes can be used as a part of a diagnostic test kit for identifying cells or tissue which misexpress (e.g., over- or under-express) a target polypeptide of the subject technology, or which have greater or fewer copies of a target gene of the subject technology. For example, a level of a target polypeptide-encoding nucleic acid in a sample of cells from a subject may be detected, the amount of mRNA transcript of a gene encoding a target polypeptide may be determined, or the presence of mutations or deletions of a target gene of the subject technology may be assessed.

The subject technology further encompasses nucleic acid molecules that differ from the nucleic acid sequences of the gene of the $Ca^{2+}$ release-stabilizing molecules of the subject technology, e.g., FKBP1b gene, due to degeneracy of the genetic code and which thus encode the same proteins as those encoded by the gene of the $Ca^{2+}$ release-stabilizing molecules, e.g., FKBP1b gene.

It will be appreciated by those skilled in the art that DNA sequence polymorphisms can lead to changes in the amino acid sequences of the proteins encoded by the genes of the $Ca^{2+}$ release-stabilizing molecules of the instant disclosure. Such genetic polymorphism in, for example, the FKBP1b gene, may exist among individuals within a population due to natural allelic variation. An allele is one of a group of genes which occur alternatively at a given genetic locus. In addition it will be appreciated that DNA polymorphisms that affect RNA expression levels can also exist that may affect the overall expression level of that gene (e.g., by affecting regulation or degradation). As used herein, the phrase "allelic variant" includes a nucleotide sequence which occurs at a given locus or to a polypeptide encoded by the nucleotide sequence. As used herein, the terms "gene" and "recombinant gene" refer to nucleic acid molecules which include an open reading frame encoding a target polypeptide of the subject technology.

Nucleic acid molecules corresponding to natural allelic variants and homologues of the gene to the $Ca^{2+}$ release-stabilizing molecules or genes encoding the $Ca^{2+}$ release-stabilizing molecules can be isolated based on their homology to the gene of the $Ca^{2+}$ release-stabilizing molecules using the cDNAs disclosed herein, or a portion thereof, as a hybridization probe according to standard hybridization techniques under stringent hybridization conditions. Nucleic acid molecules corresponding to natural allelic variants and homologues of the target genes of the subject technology can further be isolated by mapping to the same chromosome or locus as the target genes or genes encoding the target proteins of the subject technology.

In another embodiment, an isolated nucleic acid molecule of the subject technology is at least 15, 20, 25, 30, 50, 100, 150, 200, 250, 300, 350, 400, 450, 500, 550, 600, 650, 700, 750, 800, 850, 900, 950, 1000, 1100, 1200, 1300, 1400, 1500, 1600, 1700, 1800, 1900, 2000 or more nucleotides in length and hybridizes under stringent conditions to a nucleic acid molecule corresponding to a nucleotide sequence of a target gene or gene encoding a target protein of the subject technology. As used herein, the term "hybridizes under stringent conditions" is intended to describe conditions for hybridization and washing under which nucleotide sequences at least 60% sequence identity (over their entire lengths) to each other typically remain hybridized to each other. Generally, percent homology or identity is based on two polynucleotide strands that are comparable in length the percent value reflects homology throughout the length of the two strands. Preferably, the conditions are such that sequences at least about 70%, more preferably at least about 80%, even more preferably at least about 85% or 90% homologous to each other (over their entire lengths or throughout their lengths) typically remain hybridized to each other. Such stringent conditions are known to those skilled in the art and can be found in Current Protocols in Molecular Biology, John Wiley & Sons, N.Y. (1989), 6.3.1-6.3.6. A preferred, non-limiting example of stringent hybridization conditions are hybridization in 6× sodium chloride/sodium citrate (SSC) at about 45° C., followed by one or more washes in 0.2×SSC, 0.1% SDS at 50° C., preferably at 55° C., more preferably at 60° C., and even more preferably at 65° C. Preferably, an isolated nucleic acid molecule of the subject technology that hybridizes under stringent conditions to the sequence of the gene of the $Ca^{2+}$ release-stabilizing molecules, e.g., FKBP1b gene. As used herein, a "naturally-occurring" nucleic acid molecule includes an RNA or DNA molecule having a nucleotide sequence that occurs in nature (e.g. encodes a natural protein).

In addition to naturally-occurring allelic variants of the target gene and gene encoding a target protein of the subject technology sequences that may exist in the population, the skilled artisan will further appreciate that changes can be introduced by mutation into the nucleotide sequences of the target genes or genes encoding the target proteins of the subject technology, thereby leading to changes in the amino acid sequence of the encoded proteins, without altering the functional activity of these proteins. For example, nucleotide substitutions leading to amino acid substitutions at "non-essential" amino acid residues can be made. A "non-essential" amino acid residue is a residue that can be altered from the wild-type sequence of a protein without altering the biological activity, whereas an "essential" amino acid residue is required for biological activity. For example, amino acid residues that are conserved among allelic variants or homologs of a gene (e.g., among homologs of a gene from different species) are predicted to be particularly unamenable to alteration.

Accordingly, another aspect of the subject technology pertains to nucleic acid molecules encoding a target protein of the subject technology that contain changes in amino acid residues that are not essential for activity. Such proteins differ in amino acid sequence from the target proteins encoded by the gene of the $Ca^{2+}$ release-stabilizing molecules yet retain the same biological activity. In one embodiment, the protein comprises an amino acid sequence at least about 60%, 65%, 70%, 75%, 80%, 85%, 90%, 95%, 98% or more homologous or identical to a target protein of the subject technology.

An isolated nucleic acid molecule encoding a protein homologous to a target protein of the subject technology can be created by introducing one or more nucleotide substitutions, additions or deletions into the nucleotide sequence of the gene encoding the target protein, such that one or more amino acid substitutions, additions or deletions are introduced into the encoded protein. Mutations can be introduced into the gene of the $Ca^{2+}$ release-stabilizing molecules, e.g., FKBP1b gene, of the subject technology by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of a coding sequence of a gene of the subject technology, such as by saturation mutagenesis, and the resultant mutants can be screened for biological activity to identify mutants that retain activity. Following mutagenesis, the encoded protein can be expressed recombinantly and the activity of the protein can be determined.

In yet another embodiment, the nucleic acid molecules of the present subject technology can be modified at the base moiety, sugar moiety or phosphate backbone to improve, e.g., the stability, hybridization, or solubility of the molecule. For example, the deoxyribose phosphate backbone of the nucleic acid molecules can be modified to generate peptide nucleic acids (see Hyrup B. et al. (1996) Bioorganic & Medicinal Chemistry 4 (1): 5-23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup B. et al. (1996) supra; Perry-O'Keefe et al. Proc. Natl. Acad. Sci. 93: 14670-675.

In other embodiments, the oligonucleotide may include other appended groups such as peptides (e.g., for targeting host cell receptors in vivo), or agents facilitating transport across the cell membrane (see, e.g., Letsinger et al. (1989) Proc. Natl. Acad. Sci. USA 86:6553-6556; Lemaitre et al. (1987) Proc. Natl. Acad. Sci. USA 84:648-652; PCT Publication No. WO88/09810) or the blood-brain barrier (see, e.g., PCT Publication No. WO89/10134). In addition, oligonucleotides can be modified with hybridization-triggered cleavage agents (See, e.g., Krol et al. (1988) Bio-Techniques 6:958-976) or intercalating agents. (See, eg., Zon (1988) Pharm. Res. 5:539-549). To this end, the oligonucleotide may be conjugated to another molecule, (e.g., a peptide, hybridization triggered cross-linking agent, transport agent, or hybridization-triggered cleavage agent). Finally, the oligonucleotide may be detectably labeled, either such that the label is detected by the addition of another reagent (e.g. a substrate for an enzymatic label), or is detectable immediately upon hybridization of the nucleotide (e.g., a radioactive label or a fluorescent label (e.g., a molecular beacon, as described in U.S. Pat. No. 5,876,930.

II. Isolated Proteins and Antibodies

One aspect of the subject technology pertains to isolated target proteins i.e., the $Ca^{2+}$ release-stabilizing molecules, e.g., Fkbp1a, Fkbp1b variant_a, Fkbp1b variant_b, Junctophilin 3, Junctophilin 4 and Calmodulin 3, and biologically or functionally active portions thereof suitable for use as therapeutic molecules for stabilizing calcium release from ryanodine receptors (RyRs), inosital triphosphate receptors (InsP3Rs). Alternatively, the isolated target proteins i.e., the $Ca^{2+}$ release-stabilizing molecules, e.g., Fkbp1a, Fkbp1b variant_a, Fkbp1b variant_b, Junctophilin 3, Junctophilin 4 and Calmodulin 3, and biologically or functionally active portions thereof suitable for use are used as immunogens to raise anti-target protein antibodies. In one embodiment, native target proteins can be isolated from cells or tissue sources by an appropriate purification scheme using standard protein purification techniques. In another embodiment, target proteins are produced by recombinant DNA techniques. Alternative to recombinant expression, a target protein or polypeptide can be synthesized chemically using standard peptide synthesis techniques.

An "isolated" or "purified" protein or biologically active portion thereof is substantially free of cellular material or other contaminating proteins from the cell or tissue source from which the target protein is derived, or substantially free from chemical precursors or other chemicals when chemically synthesized. The language "substantially free of cellular material" includes preparations of target protein in which the protein is separated from cellular components of the cells from which it is isolated or recombinantly produced. In one embodiment, the language "substantially free of cellular material" includes preparations of target protein having less than about 30% (by dry weight) of non-target protein (also referred to herein as a "contaminating protein"), more preferably less than about 20% of non-target protein, still more preferably less than about 10% of non-target protein, and most preferably less than about 5% non-target protein. When the target protein or biologically active portion thereof is recombinantly produced, it is also preferably substantially free of culture medium, i.e., culture medium represents less than about 20%, more preferably less than about 10%, and most preferably less than about 5% of the volume of the protein preparation.

The language "substantially free of chemical precursors or other chemicals" includes preparations of target protein in which the protein is separated from chemical precursors or other chemicals which are involved in the synthesis of the protein. In one embodiment, the language "substantially free of chemical precursors or other chemicals" includes preparations of protein having less than about 30% (by dry weight) of chemical precursors or non-protein chemicals, more preferably less than about 20% chemical precursors or non-protein chemicals, still more preferably less than about 10% chemical precursors or non-protein chemicals, and most preferably less than about 5% chemical precursors or non-protein chemicals.

As used herein, a "biologically active portion" or "functional fragment" (as used interchangeably) of a target protein includes a fragment of a target protein comprising amino acid sequences sufficiently homologous to or derived from the amino acid sequence of the target protein, which include fewer amino acids than the full length target proteins, and exhibit at least one activity of a target protein, i.e., $Ca^{2+}$ release-stabilizing activity on RyRs or InsP3Rs. Typically, biologically active portions comprise a domain or motif with at least one activity of the target protein. A biologically active portion of a target protein can be a polypeptide which is, for example, 10, 25, 50, 100, 200 or more amino acids in length. Biologically active portions of a target protein can be used as targets for developing agents which modulate a target protein-mediated activity.

In a preferred embodiment, target protein is encoded by the gene of the $Ca^{2+}$ release-stabilizing molecules. In other embodiments, the target protein is substantially homologous to a target protein encoded by the genes of the $Ca^{2+}$ release-stabilizing molecules, e.g., FKBP1b gene, and retains the functional activity of the target protein, yet differs in amino acid sequence due to natural allelic variation or mutagenesis, as described in detail in subsection I above. Accordingly, in another embodiment, the target protein is a protein which comprises an amino acid sequence with at least about 60%, 65%, 70%, 75%, 80%, 85%, 90%, 95%, 98% or more sequence identity to the amino acid sequence encoded by the genes of the $Ca^{2+}$ release-stabilizing molecules, e.g., FKBP1b gene.

To determine the percent identity of two amino acid sequences or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, or 90% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch (J. Mat. Biol. (48):444-453 (1970)) algorithm which has been incorporated into the GAP program in the GCG software package, using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package, using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Meyers and W. Miller (CABIOS, 4:11-17 (1989)) which has been incorporated into the ALIGN program (version 2.0), using a PAM120 weight residue table, a gap length penalty of 12 and a gap penalty of 4.

The nucleic acid and protein sequences of the present subject technology can further be used as a "query sequence" to perform a search against public databases to, for example, identify other family members or related sequences. Such searches can be performed using the NBLAST and XBLAST programs (version 2.0) of Altschul, et al. (1990) J. Mol. Biol. 215:403-10. BLAST nucleotide searches can be performed with the NBLAST program, score=100, wordlength=12 to obtain nucleotide sequences homologous to nucleic acid molecules of the subject technology. BLAST protein searches can be performed with the XBLAST program, score=50, wordlength=3 to obtain amino acid sequences homologous to target protein molecules of the subject technology. To obtain gapped alignments for comparison purposes, Gapped BLAST can be utilized as described in Altschul et al., (1997) Nucleic Acids Res. 25(17):3389-3402. When utilizing BLAST and Gapped BLAST programs, the default parameters of the respective programs (e.g., XBLAST and NBLAST) can be used.

The subject technology also provides chimeric or fusion target proteins. As used herein, a target "chimeric protein" or "fusion protein" comprises a target polypeptide operatively linked to a non-target polypeptide. A "target polypeptide" includes a polypeptide having an amino acid sequence encoded by the genes of the $Ca^{2+}$ release-stabilizing molecules, e.g., FKBP1b gene, whereas a "non-target polypeptide" includes a polypeptide having an amino acid sequence corresponding to a protein which is not substantially homologous to the target protein, e.g., a protein which is different from target protein and which is derived from the same or a different organism. Within a target fusion protein the polypeptide can correspond to all or a portion of a target protein. In a preferred embodiment, a target fusion protein comprises at least one biologically active portion of a target protein. Within the fusion protein, the term "operatively linked" is intended to indicate that the target polypeptide and the non-target polypeptide are fused in-frame to each other. The non-target polypeptide can be fused to the N-terminus or C-terminus of the target polypeptide.

For example, in one embodiment, the fusion protein is a GST-target fusion protein in which the target sequences are fused to the C-terminus of the GST sequences. Such fusion proteins can facilitate the purification of recombinant target proteins.

In another embodiment, the fusion protein is a target protein containing a heterologous signal sequence at its N-terminus. In certain host cells (e.g., mammalian host cells), expression and/or secretion of target proteins can be increased through use of a heterologous signal sequence. Such signal sequences are well known in the art.

The target fusion proteins of the subject technology can be incorporated into pharmaceutical compositions and administered to a subject in vivo, as described herein. The target fusion proteins can be used to affect the bioavailability of a target protein substrate. Use of target fusion proteins may be useful therapeutically for the treatment of disorders (e.g., AD, MCI or other cognitive impairments) caused by, for example, (i) aberrant modification or mutation of a gene encoding a target protein; (ii) mis-regulation of the target protein-encoding gene; and (iii) aberrant post-translational modification of a target protein.

Moreover, the target-fusion proteins of the subject technology can be used as immunogens to produce anti-target protein antibodies in a subject, to purify target protein ligands and in screening assays to identify molecules which inhibit the interaction of a target protein with a target protein substrate.

Preferably, a target chimeric or fusion protein of the subject technology is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, Current Protocols in Molecular Biology, eds. Ausubel et al. John Wiley & Sons: 1992). Moreover, many expression vectors are commercially available that already encode a fusion moiety (e.g., a GST polypeptide). A target protein-encoding nucleic acid can be cloned into such an expression vector such that the fusion moiety is linked in-frame to the target protein.

A signal sequence can be used to facilitate secretion and isolation of the secreted protein or other proteins of interest. Signal sequences are typically characterized by a core of hydrophobic amino acids which are generally cleaved from the mature protein during secretion in one or more cleavage events. Such signal peptides contain processing sites that allow cleavage of the signal sequence from the mature proteins as they pass through the secretory pathway. Thus, the subject technology pertains to the described polypeptides having a signal sequence, as well as to polypeptides from which the signal sequence has been proteolytically cleaved (i.e., the cleavage products). In one embodiment, a nucleic acid sequence encoding a signal sequence can be operably linked in an expression vector to a protein of interest, such as a protein which is ordinarily not secreted or is otherwise difficult to isolate. The signal sequence directs secretion of the protein, such as from a eukaryotic host into which the expression vector is transformed, and the signal sequence is subsequently or concurrently cleaved. The protein can then be readily purified from the extracellular medium by art recognized methods. Alternatively, the signal sequence can be linked to the protein of interest using a sequence which facilitates purification, such as with a GST domain.

The present subject technology also pertains to variants of the target proteins of the subject technology which function as either agonists (mimetics) or as antagonists to the target proteins. Variants of the target proteins can be generated by mutagenesis, e.g., discrete point mutation or truncation of a target protein. An agonist of the target proteins can retain substantially the same, or a subset, of the biological activities of the naturally occurring form of a target protein. An antagonist of a target protein can inhibit one or more of the activities of the naturally occurring form of the target protein by, for example, competitively modulating an activity of a target protein. Thus, specific biological effects can be elicited by treatment with a variant of limited function. In one embodiment, treatment of a subject with a variant having a subset of the biological activities of the naturally occurring form of the protein has fewer side effects in a subject relative to treatment with the naturally occurring form of the target protein.

Variants of a target protein which function as either target protein agonists (mimetics) or as target protein antagonists can be identified by screening combinatorial libraries of mutants, e.g., truncation mutants, of a target protein for target protein agonist or antagonist activity. In one embodiment, a variegated library of target protein variants is generated by combinatorial mutagenesis at the nucleic acid level and is encoded by a variegated gene library. A variegated library of target protein variants can be produced by, for example, enzymatically ligating a mixture of synthetic oligonucleotides into gene sequences such that a degenerate set of potential target protein sequences is expressible as individual polypeptides, or alternatively, as a set of larger fusion proteins (e.g., for phage display) containing the set of target protein sequences therein. There are a variety of methods which can be used to produce libraries of potential target protein variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential target protein sequences. Methods for synthesizing degenerate oligonucleotides are known in the art (see, e.g., Narang, S. A. (1983) Tetrahedron 39:3; Itakura et al. (1984) Annu. Rev. Biochem. 53:323; Itakura et al. (1984) Science 198:1056; Ike et al. (1983) Nucleic Acid Res. 11:477).

In addition, libraries of fragments of a protein coding sequence corresponding to a target protein of the subject technology can be used to generate a variegated population of target protein fragments for screening and subsequent selection of variants of a target protein. In one embodiment, a library of coding sequence fragments can be generated by treating a double stranded PCR fragment of a target protein coding sequence with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal, C-terminal and internal fragments of various sizes of the target protein.

Several techniques are known in the art for screening gene products of combinatorial libraries made by point mutations or truncation, and for screening cDNA libraries for gene products having a selected property. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a technique which enhances the frequency of functional mutants in the libraries, can be used in combination with the screening assays to identify target variants (Arkin and Yourvan (1992) Proc. Natl. Acad. Sci. USA 89:7811-7815; Delgrave et al. (1993) Protein Engineering 6(3):327-331).

An isolated target protein, or a portion or fragment thereof, can be used as an immunogen to generate antibodies that bind target proteins using standard techniques for polyclonal and monoclonal antibody preparation. A full-length target protein can be used or, alternatively, the subject technology provides antigenic peptide fragments of these proteins for use as immunogens. The antigenic peptide of a target protein comprises at least 8 amino acid residues of an amino acid sequence encoded by the FKBP1b gene, and encompasses an epitope of a target protein such that an antibody raised against the peptide forms a specific immune complex with the target protein. Preferably, the antigenic peptide comprises at least 10 amino acid residues, more preferably at least 15 amino acid residues, even more preferably at least 20 amino acid residues, and most preferably at least 30 amino acid residues.

III. Recombinant Expression Vectors and Host Cells

Another aspect of the subject technology pertains to vectors, preferably expression vectors, containing a nucleic acid encoding a target protein, i.e., a $Ca^{2+}$ release-stabilizing molecule, e.g., Fkbp1a, Fkbp1b variant_a, Fkbp1b variant_b, Junctophilin 3, Junctophilin 4 and Calmodulin 3 and biologically or functionally active portions thereof, of the subject technology. As used herein, the term "vector" includes a nucleic acid molecule capable of transporting another nucleic acid to which it has been linked. One type of vector is a "plasmid", which includes a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the subject technology is intended to include such other forms of expression vectors, such as viral vectors (e.g. replication defective retroviruses, adenoviruses and adeno-associated viruses), which serve equivalent functions.

The recombinant expression vectors of the subject technology comprise a nucleic acid of the subject technology in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel; Gene Expression Technology: Methods in Enzymology 185, Academic Press, San Diego, Calif. (1990). Regulatory sequences include those which direct constitutive expression of a nucleotide sequence in many types of host cells and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, and the like. The expression vectors of the subject technology can be introduced into host cells to thereby produce proteins or peptides, including fusion proteins or peptides, encoded by nucleic acids as described herein (e.g., target proteins, mutant forms of target proteins, fusion proteins, and the like).

The recombinant expression vectors of the subject technology can be designed for expression of target proteins in prokaryotic or eukaryotic cells. For example, target proteins can be expressed in bacterial cells such as E. coli, insect cells (using baculovirus expression vectors) yeast cells or mammalian cells. Suitable host cells are discussed further in Goeddel, Gene Expression Technology: Methods in Enzymology 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in E. coli with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) Gene 67:31-40), pMAL (New England Biolabs, Beverly, Mass.) and pRITS (Pharmacia, Piscataway, N.J.) which fuse glutathione S-transferase (GST), maltose E binding protein, or protein A, respectively, to the target recombinant protein.

Purified fusion proteins can be utilized in target activity assays, (e.g., direct assays or competitive assays described in detail below), or to generate antibodies specific for target proteins, for example.

Examples of suitable inducible non-fusion E. coli expression vectors include pTrc (Amann et al., (1988) Gene 69:301-315) and pET 11d (Studier et al., Gene Expression Technology: Methods in Enzymology 185, Academic Press, San Diego, Calif. (1990) 60-89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21(DE3) or HMS174 (DE3) from a resident prophage harboring a T7 gn1 gene under the transcriptional control of the lacUV 5 promoter.

One strategy to maximize recombinant protein expression in E. coli is to express the protein in a host bacteria with an impaired capacity to proteolytically cleave the recombinant protein (Gottesman, S., Gene Expression Technology: Methods in Enzymology 185, Academic Press, San Diego, Calif. (1990) 119-128). Another strategy is to alter the nucleic acid sequence of the nucleic acid to be inserted into an expression vector so that the individual codons for each amino acid are those preferentially utilized in E. coli (Wada et al., (1992) Nucleic Acids Res. 20:2111-2118). Such alteration of nucleic acid sequences of the subject technology can be carried out by standard DNA synthesis techniques.

In another embodiment, the target protein expression vector is a yeast expression vector. Examples of vectors for expression in yeast S. cerevisiae include pYepSec1 (Baldari, et al., (1987) Embo J. 6:229-234), pMFa (Kurjan and Herskowitz, (1982) Cell 30:933-943), pJRY88 (Schultz et al., (1987) Gene 54:113-123), pYES2 (Invitrogen Corporation, San Diego, Calif.), and picZ (InVitrogen Corp, San Diego, Calif.).

Alternatively, target proteins of the subject technology can be expressed in insect cells using baculovirus expression vectors. Baculovirus vectors available for expression of proteins in cultured insect cells (e.g., Sf 9 cells) include the pAc series (Smith et al. (1983) Mol. Cell. Biol. 3:2156-2165) and the pVL series (Lucklow and Summers (1989) Virology 170:31-39).

In yet another embodiment, a nucleic acid of the subject technology is expressed in mammalian cells using a mammalian expression vector. Examples of mammalian expression vectors include pCDM8 (Seed, B. (1987) Nature 329:840) and pMT2PC (Kaufman et al. (1987) EMBO J. 6:187-195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook, J., Fritsh, E. F., and Maniatis, T. Molecular Cloning: A Laboratory Manual. 2nd, ed., Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) Genes Dev. 1:268-277), lymphoid-specific promoters (Calame and Eaton (1988) Adv. Immunol. 43:235-275), in particular promoters of T cell receptors (Winoto and Baltimore (1989) EMBO J. 8:729-733) and immunoglobulins (Banerji et al. (1983) Cell 33:729-740; Queen and Baltimore (1983) Cell 33:741-748), neuron-specific promoters (e.g., the neurofilament promoter; Byrne and Ruddle (1989) Proc. Natl. Acad. Sci. USA 86:5473-5477), pancreas-specific promoters (Edlund et al. (1985) Science 230:912-916), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss (1990) Science 249:374-379) and the fetoprotein promoter (Campes and Tilghman (1989) Genes Dev. 3:537-546).

Another aspect of the subject technology pertains to host cells into which a nucleic acid molecule of the subject technology is introduced, e.g., genes of the $Ca^{2+}$ release-stabilizing molecules, e.g., FKBP1b gene within a recombinant expression vector or a nucleic acid molecule of the subject technology containing sequences which allow it to homologously recombine into a specific site of the host cell's genome. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, a target protein of the subject technology can be expressed in bacterial cells such as *E. coli*, insect cells, yeast or mammalian cells (such as Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (Molecular Cloning: A Laboratory Manual. 2nd, ed., Cold Spring Harbor Laboratory, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable target (e.g., resistance to antibiotics) is generally introduced into the host cells along with the gene of interest. Preferred selectable targets include those which confer resistance to drugs, such as G418, hygromycin and methotrexate. Nucleic acid encoding a selectable target can be introduced into a host cell on the same vector as that encoding a target protein or can be introduced on a separate vector. Cells stably transfected with the introduced nucleic acid can be identified by drug selection (e.g., cells that have incorporated the selectable target gene will survive, while the other cells die).

A host cell of the subject technology, such as a prokaryotic or eukaryotic host cell in culture, can be used to produce (i.e., express) a target protein. Accordingly, the subject technology further provides methods for producing a target protein using the host cells of the subject technology. In one embodiment, the method comprises culturing the host cell of subject technology (into which a recombinant expression vector encoding a target protein has been introduced) in a suitable medium such that a target protein of the subject technology is produced. In another embodiment, the method further comprises isolating a target protein from the medium or the host cell. The host cells of the subject technology can also be used to produce non-human transgenic animals. For example, in one embodiment, a host cell of the subject technology is a fertilized oocyte or an embryonic stem cell into which target-protein-coding sequences have been introduced. Such host cells can then be used to create non-human transgenic animals in which exogenous sequences encoding a target protein of the subject technology have been introduced into their genome or homologous recombinant animals in which endogenous sequences encoding the target proteins of the subject technology have been altered. Such animals are useful for studying the function and/or activity of a target protein and for identifying and/or evaluating modulators of target protein activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, and the like. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, a "homologous recombinant animal" is a non-human animal, preferably a mammal, more preferably a mouse, in which an endogenous FKBP1b gene has been altered by homologous recombination between the endogenous gene and an exogenous DNA molecule introduced into a cell of the animal, e.g., an embryonic cell of the animal, prior to development of the animal.

A transgenic animal of the subject technology can be created by introducing a target-encoding nucleic acid into the male pronuclei of a fertilized oocyte, e.g., by microinjection, retroviral infection, and allowing the oocyte to develop in a pseudopregnant female foster animal. Intronic sequences and polyadenylation signals can also be included in the transgene to increase the efficiency of expression of the transgene. A tissue-specific regulatory sequence(s) can be operably linked to a transgene to direct expression of a target protein to particular cells. Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., Manipulating the Mouse Embryo, (Cold Spring Harbor Laboratory Press, Cold Spring Harbor, N.Y., 1986). Similar methods are used for production of other transgenic animals. A transgenic founder animal can be identified based upon the presence of a transgene of the subject technology in its genome and/or expression of mRNA corresponding to a gene of the subject technology in tissues or cells of the animals. A transgenic founder animal can then be used to breed additional animals carrying the transgene. Moreover, transgenic animals carrying a transgene encoding a target protein can further be bred to other transgenic animals carrying other transgenes.

IV. Pharmaceutical Compositions

The molecules of the subject technology i.e. the $Ca^{2+}$ release-stabilizing molecules (including polypeptides, polynucleotides, small molecules or large molecules that can bind to and enhance the activity or stability of the proteins of the subject technology (including Fkbp1a, Fkbp1b variant_a, Fkbp1b variant_b, Junctophilin 3, Junctophilin 4 and Calmodulin 3, ryanodine receptors (RyRs), inositol triphosphate receptors (InsP3Rs)) can be incorporated into pharmaceutical compositions suitable for administration. Such compositions typically comprise the nucleic acid molecule, protein, or small molecules and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The subject technology includes methods for preparing pharmaceutical compositions for modulating the expression or activity of a ryanodine receptor (RyR), inositol triphosphate receptor (InsP3R) or a polypeptide or nucleic acid corresponding to a $Ca^{2+}$ release-stabilizing molecule of the subject technology. Such methods comprise formulating a pharmaceutically acceptable carrier with an agent which modulates expression or activity of a polypeptide or nucleic acid corresponding to a target of the subject technology. Such compositions can further include additional active agents. Thus, the subject technology further includes methods for preparing a pharmaceutical composition by formulating a pharmaceutically acceptable carrier with an agent which modulates expression or activity of a polypeptide or nucleic acid corresponding to a target of the subject technology and one or more additional active compounds.

V. Drug Screening Assays

The subject technology also provides methods (also referred to herein as "screening assays") for identifying modulators, i.e., candidate or test compounds or agents (e.g. peptides, peptidomimetics, peptoids, small molecules or large molecules or other drugs) which (a) bind to the target (i.e., FKBP1a, FKBP1b, junctophilin 3, junctophilin 4, calmodulin 3, RyRs, InsP3Rs, a variant thereof or a functional fragment thereof), or (b) have a modulatory (e.g., stimulatory or inhibitory) effect on the activity of the target or, more specifically, (c) have a modulatory effect on the interactions of the target with one or more of its natural substrates (e.g., peptide, protein, hormone, co-factor, or nucleic acid), or (d) have a modulatory effect on the expression of the target. Such assays typically comprise a reaction between the target and one or more assay components. The other components may be either the test compound itself, or a combination of test compound and a natural binding partner of the target.

The test compounds of the present subject technology may be obtained from any available source, including systematic libraries of natural and/or synthetic compounds. Test compounds may also be obtained by any of the numerous approaches in combinatorial library methods known in the art, including: biological libraries; peptoid libraries (libraries of molecules having the functionalities of peptides, but with a novel, non-peptide backbone which are resistant to enzymatic degradation but which nevertheless remain bioactive; see, e.g., Zuckermann et al., 1994, J. Med. Chem. 37:2678-85); spatially addressable parallel solid phase or solution phase libraries; synthetic library methods requiring deconvolution; the 'one-bead one-compound' library method; and synthetic library methods using affinity chromatography selection. The biological library and peptoid library approaches are limited to peptide libraries, while the other four approaches are applicable to peptide, non-peptide oligomer or small molecule libraries of compounds (Lam, 1997, Anticancer Drug Des. 12:145).

In one exemplary assay format, the ability of a molecule to modulate the expression and/or the function of a gene or protein of the subject technology is assayed by monitoring the expression and/or function of said gene or protein in cell lines which were exposed to the molecule and comparing said expression to that in cell lines which were not exposed to the molecule. Such monitoring can be done using standard procedures such those disclosed in Sambrook et al., (1989) Molecular Cloning—A Laboratory Manual, Cold Spring Harbor Laboratory Press).

Molecules that are assayed in the above methods can be randomly selected or rationally selected or designed. As used herein, a molecule is said to be randomly selected when the molecule is chosen randomly without considering the specific sequences involved in the association of the a protein of the subject technology alone or with its associated substrates, binding partners, etc. An example of randomly selected molecules is the use a chemical library or a peptide combinatorial library, or a growth broth of an organism.

VI. Routes of Administration

A pharmaceutical composition or polypeptide, polynucleotide, small molecule or large molecule of the subject technology is formulated to be compatible with its intended route of administration. Examples of routes of administration and dosage forms of such formulations are shown in the Table below.

| | Routes of administration/Dosage forms | | | |
|---|---|---|---|---|
| Oral | Digestive tract (enteral) | Solids | Pill, Tablet, Capsule, Time release technology, Osmotic controlled release capsule (OROS) |
| | | Liquids | Solution, Softgel, Suspension, Emulsion, Syrup, Elixir, Tincture, Hydrogel |
| | Buccal/ Sublabial/ Sublingual | Solids | Orally Disintegrating Tablet (ODT), Film, Lollipop, Lozenges, Chewing gum |
| | | Liquids | Mouthwash, Toothpaste, Ointment, Oral spray |
| | Respiratory tract | Solids | Smoking device Dry Powder Inhaler (DPI) |
| | | Liquids | pressurized Metered Dose Inhaler (pMDI), Nebulizer, Vaporizer |

| Routes of administration/Dosage forms | | |
|---|---|---|
| | Gas | Oxygen mask, Oxygen concentrator, Anaesthetic machine, Relative analgesia machine |
| Ophthalmic/ Otologic/ Nasal | Nasal spray, Ear drops, Eye drops, Ointment, Hydrogel, Nanosphere suspension, Mucoadhesive microdisc (microsphere tablet) | |
| Urogenital | Ointment, Pessary (vaginal suppository), Vaginal ring, Vaginal douche, Intrauterine device (IUD), Extra-amniotic infusion, Intravesical infusion | |
| Rectal (enteral) | Ointment, Suppository, Enema (Solution, Hydrogel), Murphy drip, Nutrient enema | |
| Dermal | Ointment, Liniment, Paste, Film, Hydrogel, Liposomes, Transfersome vesicles, Cream, Lotion, Lip balm, Medicated shampoo, Dermal patch, Transdermal patch, Transdermal spray, Jet injector | |
| Injection/ Infusion (into tissue/blood) | Skin | Intradermal, Subcutaneous, Transdermal implant |
| | Organs | Intracavernous, Intravitreal, Intra-articular, or intrasynovial injection, Transscleral |
| | Central nervous system | Intracerebral, Intrathecal, Epidural |
| | Circulatory/ Musculoskeletal | Intravenous, Intracardiac, Intramuscular, Intraosseous, Intraperitoneal, Nanocell injection |

Alternative or additional examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifingal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a fragment of a target protein) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein includes physically discrete units suited as unitary dosages for the subject to be treated; each unit containing a predetermined quantity of active compound calculated to produce the desired therapeutic effect in association with the required pharmaceutical carrier. The specification for the dosage unit forms of the subject technology are dictated by and directly dependent on the unique characteristics of the active compound and the particular therapeutic effect to be achieved, and the limitations inherent in the art of compounding such an active compound for the treatment of individuals.

Toxicity and therapeutic efficacy of the molecules of the subject technology can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the subject technology, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

The nucleic acid molecules of the subject technology can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) Proc. Natl. Acad. Sci. USA 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

VI. Methods of Treatment

The subject technology provides for both prophylactic and therapeutic methods of treating Alzheimer's Disease (AD), early-stage AD, elevated risk of AD, mild cognitive impairment (MCI), or other forms of age-related cognitive decline in a subject. In some embodiments, the subject technology provides a method of treating Alzheimer's Disease (AD), early-stage AD, elevated risk of AD, mild cognitive impairment (MCI), or other forms of age-related cognitive decline in a subject in need thereof, comprising administering to the subject a molecule that promotes calcium-release stabilization in ryanodine receptors (RyR) and/or inositol triphosphate receptors (InsP3R) in brain cells.

In some other embodiments, the subject technology provides a method of treating Alzheimer's Disease (AD), early-stage AD, elevated risk of AD, mild cognitive impairment (MCI), or other forms of age-related cognitive decline in a subject in need thereof, comprising administering to the subject a calcium ($Ca^{2+}$)-release stabilizing molecule, wherein said molecule induces reduction, inhibition or reversal of $Ca^{2+}$ dysregulation in brain cells of the subject.

In an embodiment, the subject technology also provides methods of preventing the development AD or other cognitive impairments associated with $Ca^{2+}$ dysregulation in a subject. These methods involve, for targets that are significantly decreased in expression or activity, the administration of that target protein, or the introduction of mRNA or DNA corresponding to the decreased target (e.g., by gene therapy), to thereby increase the levels of the target protein in the subject. In this manner, the development AD or other cognitive impairments associated with $Ca^{2+}$ dysregulation in a subject can be prevented.

With regards to both prophylactic and therapeutic methods of treatment, such treatments may be specifically tailored or modified, based on knowledge obtained from the field of pharmacogenomics. "Pharmacogenomics", as used herein, includes the application of genomics technologies such as gene sequencing, statistical genetics, and gene expression analysis to drugs in clinical development and on the market. More specifically, the term refers the study of how a subject's genes determine his or her response to a drug (e.g., a subject's "drug response phenotype", or "drug response genotype".) Thus, another aspect of the subject technology provides methods for tailoring an individual's prophylactic or therapeutic treatment with either the target molecules of the present subject technology or target modulators according to that individual's drug response genotype. Pharmacogenomics allows a clinician or physician to target prophylactic or therapeutic treatments to subjects who will most benefit from the treatment and to avoid treatment of subjects who will experience toxic drug-related side effects.

In one aspect, the subject technology provides a method for preventing in a subject, a disease or condition (e.g., AD or other cognitive impairments) associated with decreased target expression or activity or associated with aberrant target activity (e.g., calcium release dysregulation in RyRs and/or InsP3Rs), by administering to the subject a molecule or an agent which modulates target protein expression or at least one target protein activity in a way that the course of the $Ca^{2+}$-dysregulation associated with aging and/or AD phenotype is stopped or reversed. Subjects at risk for a disease which is caused or contributed to by decreased target expression or activity can be identified by, for example, any or a combination of diagnostic or prognostic assays as described herein. Administration of a prophylactic agent can occur prior to the manifestation of symptoms characteristic of the differential target protein expression, such that a disease or disorder is prevented or, alternatively, delayed in its progression. Depending on the type of target aberrancy (e.g., increase or decrease in expression level), for example, a target protein, target protein agonist or target protein antagonist agent can be used for treating the subject. The appropriate agent can be determined based on screening assays described herein. Examples of agents such as small molecules or large molecules that modulate the target molecules (e.g., $Ca^{2+}$ release-stabilizing molecules or $Ca^{2+}$ channels including RyRs and InsP3Rs) of the subject technology can be immunosuppressants such as rapamycin, and analogues of rapamycin, such as CCI-779 and analogue described in U.S. Pat. No. 5,362,718, incorporated herein by reference, FK506, macolides of FK506 and rapamycin (Dumont, F. et al., "The Immunosuppressive Macrolides FK-506 and Rapamycin Act as Reciprocal Antagonists in Murine T Cells", J. Immunol. 144: 1418-1424 (1990), synthetic amnalogues of rapamycin, FK506 (R. S. Coleman et al., "Degradation and Manipulations of the Immunosuppressant FK506: Preparation of Potential Synthetic Intermediates," Heterocycles, 28, pp. 157-161 (1989) and U.S. Pat. No. 6,200,985, each of which is hereby incorporated herein by reference) or JTV519 (K201) a 1,4-benzothiazepine drug with antiarrhythmic and cardioprotective properties (see Diabetes, Metabolic Syndrome and Obesity: Targets and Therapy 2012:5 89-99, which is hereby incorporated herein by reference).

Alternatively, the examples of molecules that can be used in the methods of the subject technology further include non-immunosuppressive ligands. The non-immunosuppressive lingand of immunophilins, junctophilins, calmoduling or calcium receptors of the subject technology can be a low molecular weight, small molecule compound having an affinity for the $Ca^{2+}$ release-stabilizing molecules or $Ca^{2+}$ receptors of the subject technology. For example, when the compound binds to a $Ca^{2+}$ release-stabilizing molecule, it can enhance its $Ca^{2+}$ release-stabilizing activity. As its name suggests, the non-immunosuppressive ligands or compounds are devoid of any significant immunosuppressive activity. Examples of a non-immunosuppressive neurolmmunophilin FKBP ligands that may be used in the method and pharmaceutical composition of the subject technology are set forth, for example, in PCT Publication WO00/09108, which is hereby incorporated herein by reference.

Another aspect of the subject technology pertains to methods of modulating the expression or activity of a target protein (i.e., a $Ca^{2+}$ release-stabilizing molecule or a $Ca^{2+}$ receptor of the subject technology) for therapeutic purposes. Accordingly, in an exemplary embodiment, the modulatory method of the subject technology involves contacting a cell with a molecule or agent that modulates the expression or activity of a target protein. A molecule or an agent that modulates the expression or activity of a target protein can be a nucleic acid or a protein, a naturally-occurring target molecule of a target protein (e.g., a target protein substrate), a target protein antibody, a target protein agonist or antagonist, a peptidomimetic of a target protein agonist or antagonist, or other small or large molecules. In one embodiment, the molecule stimulates one or more target protein. Examples of such stimulatory agents include active target protein and a nucleic acid molecule encoding target protein that has been introduced into the cell. In another embodiment, the molecule inhibits one or more target protein activities. Examples of such inhibitory molecules include antisense target protein nucleic acid molecules, anti-target protein antibodies, and target protein inhibitors. These modulatory methods can be performed in vitro (e.g., by culturing the cell with the agent) or, alternatively, in vivo (e.g., by administering the agent to a subject). As such, the present subject technology provides methods of treating an individual afflicted with a disease or disorder characterized by aberrant expression or activity of a target protein or nucleic acid molecule. In one embodiment, the method involves administering a molecule or an agent (e.g., an agent identified by a screening assay described herein), or combination of agents that modulates (e.g., upregulates or corrects) target protein expression or activity. In another embodiment, the method involves administering a target protein or nucleic acid molecule as therapy to compensate for reduced or aberrant target protein expression or activity.

Stimulation of target protein activity is desirable in situations in which target protein is abnormally downregulated and/or in which increased target protein activity is likely to have a beneficial effect. For example, stimulation of target protein activity is desirable in situations in which a target is downregulated and/or in which increased target protein activity is likely to have a beneficial effect.

In another embodiment, the subject technology provides a method of treating a subject afflicted with AD or other cognitive impairments, including providing to cells of the subject a protein with $Ca^{2+}$ release-stabilizing activity, e.g., FKBP1b. In a related embodiment, the protein is provided to the cells by providing a vector including a polynucleotide encoding the $Ca^{2+}$ release-stabilizing molecules, e.g., FKBP1b protein to the cells.

In another embodiment, the subject technology provides a method of inhibiting AD or other cognitive impairments associated with $Ca^{2+}$ dysregulation in a subject at risk for developing AD or other cognitive impairments, including stimulating the activity (in case of protein) or expression (in case of a gene) of a $Ca^{2+}$ release-stabilizing molecule, e.g., FKBP1b.

In another embodiment, the subject technology provides a method of treating a subject afflicted with AD or other cognitive impairments, including providing to cells of the subject a molecule (e.g., a polynucleotide, a protein or a small organic or large molecule) that can ligate to and stabilize Ry receptor, InsP3 receptor, or a $Ca^{2+}$ release-stabilizing molecule, e.g., FKBP1b, in said cells of the subject. In a related embodiment, the molecule can enhance the activity of the $Ca^{2+}$ release-stabilizing molecules in vivo.

VII. Predictive Medicine

The present subject technology pertains to the field of predictive medicine in which diagnostic assays and prognostic assays are used for prognostic (predictive) purposes to thereby treat an individual prophylactically.

1. Diagnostic Assays

In some embodiments, the subject technology relates to diagnostic assays for diagnosing Alzheimer's Disease (AD), early-stage AD, elevated risk of AD or mild cognitive impairment (MCI) in a patient, including obtaining a biological sample from the patient, detecting presence, quantity, or level of expression of one or more calcium-release stabilizing immunophilin, junctophilin and/or calmodulin genes in the biological sample from said patient, wherein a difference in the presence, quantity or level of expression of said one or more genes in the sample as compared to a control is indicative of Alzheimer's Disease (AD), early-stage AD, elevated risk of AD or mild cognitive impairment (MCI).

An exemplary agent for detecting target protein is an antibody capable of binding to target protein, preferably an antibody with a detectable label. Antibodies can be polyclonal, or more preferably, monoclonal. An intact antibody, or a fragment thereof (eg., Fab or F(ab')$_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells and biological fluids isolated from a subject, as well as tissues, cells and fluids present within a subject. That is, the detection method of the subject technology can be used to detect target mRNA, protein, or genomic DNA in a biological sample in vitro as well as in vivo. For example, in vitro techniques for detection of target mRNA include Northern hybridizations and in situ hybridizations. In vitro techniques for detection of target protein include enzyme linked immunosorbent assays (ELISAs), Western blots, immunoprecipitations and immunofluorescence. In vitro techniques for detection of target genomic DNA include Southern hybridizations. Furthermore, in vivo techniques for detection of target protein include introducing into a subject a labeled anti-target antibody. For example, the antibody can be labeled with a radioactive target whose presence and location in a subject can be detected by standard imaging techniques.

In one embodiment, the biological sample contains protein molecules from the patient or test subject. Alternatively, the biological sample can contain mRNA molecules from the test subject or genomic DNA molecules from the test subject. A preferred biological sample is a serum sample isolated by conventional means from a subject.

In another embodiment, the methods further involve obtaining a control biological sample (e.g., non-AD or samples showing no cognitive impairments associated with $Ca^{2+}$ dysregulation) from a control subject, contacting the control sample with a compound or agent capable of detecting target protein, mRNA, or genomic DNA, such that the presence of target protein, mRNA or genomic DNA is detected in the biological sample, and comparing the presence of target protein, mRNA or genomic DNA in the control sample with the presence of target protein, mRNA or genomic DNA in the test sample.

The subject technology includes methods that quantify expression levels in clinical samples as well as methods that determine whether a gene of interest is expressed at all or expressed above a threshold (e.g., a control threshold) in clinical samples. Thus, an assay which provides a "yes or no" result without necessarily providing quantification of gene expression is within the scope of the subject technology. The subject technology may involve quantitative or qualitative assessment of gene expression.

Various methods for detecting the level of expression of one or more genes in a sample is known in the art. For example, traditional Northern blotting, nuclease protection, RT-PCR and differential display methods may be used for detecting gene expression levels, including Taqman and flap endonuclease assays. Additional assays include array or chip hybridization-based methods, which are convenient when determining the expression levels of a larger number of genes.

In some embodiments, the subject technology may employ reverse transcription polymerase chain reaction (RT-PCR), which is a sensitive method for the detection of mRNA, including low abundant mRNAs present in clinical tissue samples. The application of fluorescence techniques to RT-PCR combined with suitable instrumentation has led to quantitative RT-PCR methods that combine amplification, detection and quantification in a closed system. Two commonly used quantitative RT-PCR techniques are the Taqman RT-PCR assay (ABI, Foster City, USA) and the Lightcycler assay (Roche, USA).

In other embodiments, the subject technology employs detection and quantification of RNA levels in real-time using nucleic acid sequence based amplification (NASBA) combined with molecular beacon detection molecules. NASBA is a singe-step isothermal RNA-specific amplification method that amplifies mRNA in a double stranded DNA environment, and this method has recently proven useful in the detection of various mRNAs, and in the detection of both viral and bacterial RNA in clinical samples.

In yet other embodiments, the subject technology uses an assay employing a flap endonuclease, such as the Invader™ assay (Third Wave Technologies). In the case of using the invader method, an invader probe containing a sequence specific to the region 3' to a target site, and a primary probe containing a sequence specific to the region 5' to the target site of a template and an unrelated flap sequence, are prepared. Cleavase is then allowed to act in the presence of these probes, the target molecule, as well as a FRET probe containing a sequence complementary to the flap sequence and an auto-complementary sequence that is labeled with both a fluorescent dye and a quencher. When the primary probe hybridizes with the template, the 3' end of the invader probe penetrates the target site, and this structure is cleaved by the Cleavase resulting in dissociation of the flap. The flap binds to the FRET probe and the fluorescent dye portion is cleaved by the Cleavase resulting in emission of fluorescence.

In another embodiment, the subject technology employs hybridization-based assays. Nucleic acid hybridization simply involves contacting a probe and target nucleic acid under conditions where the probe and its complementary target can form stable hybrid duplexes through complementary base pairing (see Lockhart et al., (1999) WO 99/32660). The nucleic acids that do not form hybrid duplexes are then washed away leaving the hybridized nucleic acids to be detected, typically through detection of an attached detectable label. It is generally recognized that nucleic acids are denatured by increasing the temperature or decreasing the salt concentration of the buffer containing the nucleic acids.

Under low stringency conditions (e.g., low temperature and/or high salt) hybrid duplexes (e.g., DNA-DNA, RNA-RNA or RNA-DNA) will form even where the annealed sequences are not perfectly complementary. Thus specificity of hybridization is reduced at lower stringency. Conversely, at higher stringency (e.g., higher temperature or lower salt) successful hybridization requires fewer mismatches. One of skill in the art will appreciate that hybridization conditions may be selected to provide any degree of stringency. In a preferred embodiment, hybridization is performed at low stringency, in this case in 6×SSPE-T at 37° C. (0.005% Triton x-100) to ensure hybridization and then subsequent washes are performed at higher stringency (e.g., 1×SSPE-T at 37° C.) to eliminate mismatched hybrid duplexes. Successive washes may be performed at increasingly higher stringency (e.g., down to as low as 0.25×SSPET at 37° C. to 50° C.) until a desired level of hybridization specificity is obtained. Stringency can also be increased by addition of agents such as formamide. Hybridization specificity may be evaluated by comparison of hybridization to the test probes with hybridization to the various controls that can be present (e.g., expression level control, normalization control, mismatch controls, etc.).

The hybridized nucleic acids are typically detected by detecting one or more labels attached to the sample nucleic acids. The labels may be incorporated by any of a number of means well known to those of skill in the art (see Lockhart et al., (1999) WO 99/32660).

When employing hybridization formats, solution-based and solid support-based assay formats may be employed. Solid supports containing oligonucleotide probes for differentially expressed genes of the subject technology can be filters, polyvinyl chloride dishes, silicon or glass based chips, etc. Such wafers and hybridization methods are widely available, for example, those disclosed by Beattie (WO 95/11755). Any solid surface to which oligonucleotides can be bound, either directly or indirectly, either covalently or non-covalently, can be used. An exemplary solid support is a high density array or DNA chip. These contain a particular oligonucleotide probe in a predetermined location on the array. Each predetermined location may contain more than one molecule of the probe, but each molecule within the predetermined location has an identical sequence. Such predetermined locations are termed features. There may be, for example, about 2, 10, 100, 1000 to 10,000; 100,000 or 400,000 of such features on a single solid support. The solid support, or the area within which the probes are attached may be on the order of a square centimeter.

Oligonucleotide probe arrays for expression monitoring can be made and used according to any techniques known in the art (see for example, Lockhart et al., (1996) Nat. Biotechnol. 14, 1675-1680; McGall et al., (1996) Proc. Nat. Acad. Sci. USA 93, 13555-13460). Such probe arrays may contain at least two or more oligonucleotides that are complementary to or hybridize to two or more of the genes described herein. Such arrays may also contain oligonucleotides that are complementary or hybridize to at least about 2, 3, 4, 5, 6, 7, 8, 9, 10, 20, 30, 50, or all of the genes described herein as being differentially expressed in AD.

Probes based on the sequences of the genes described herein may be prepared by any commonly available method. Oligonucleotide probes for assaying the tissue or cell sample are preferably of sufficient length to specifically hybridize only to appropriate, complementary genes or transcripts. Typically the oligonucleotide probes will be at least 10, 12, 14, 16, 18, 20 or 25 nucleotides in length. In some cases longer probes of at least 30, 40, or 50 nucleotides will be desirable.

As used herein, oligonucleotide sequences that are complementary to one or more of the genes described herein, refers to oligonucleotides that are capable of hybridizing under stringent conditions to at least part of the nucleotide sequence of said genes. Such hybridizable oligonucleotides will typically exhibit at least about 75% sequence identity at the nucleotide level to said genes, preferably about 80% or 85% sequence identity or more preferably about 90% or 95% or more sequence identity to said genes. In some embodiments, the oligonucleotide probes are identical to a portion of the genes disclosed herein, and usually identical in a range of 10-30 nucleotides, such as 15-20 nucleotides.

Further, with respect to arrays, one of skill in the art will appreciate that an enormous number of array designs are suitable for the practice of the subject technology, where array embodiments are desirable. The array will typically include a number of probes that specifically hybridize to the sequences of interest. See WO 99/32660 for methods of producing probes for a given gene or genes. In addition, in a preferred embodiment, the array will include one or more control probes.

High density array chips of the subject technology include "test probes." Test probes may be oligonucleotides that range from about 5 to about 500 or about 5 to about 50 nucleotides, more preferably from about 10 to about 40 nucleotides and most preferably from about 15 to about 40 nucleotides in length. In other particularly preferred embodiments the probes are about 20 to 25 nucleotides in length. In another preferred embodiment, test probes are double or single strand DNA sequences. DNA sequences are isolated or cloned from natural sources or amplified from natural sources using natural nucleic acid as templates. These probes have sequences complementary to particular subsequences of the genes whose expression they are designed to detect. Thus, the test probes are capable of specifically hybridizing to the target nucleic acid they are to detect.

In addition to test probes that bind the target nucleic acid(s) of interest, the high density array can contain a number of control probes. The control probes fall into three categories referred to herein as (1) normalization controls; (2) expression level controls; and (3) mismatch controls.

Normalization controls are oligonucleotide or other nucleic acid probes that are complementary to labeled reference oligonucleotides or other nucleic acid sequences that are added to the nucleic acid sample. The signals obtained from the normalization controls after hybridization provide a control for variations in hybridization conditions, label intensity, "reading" efficiency and other factors that may cause the signal of a perfect hybridization to vary between arrays. In a preferred embodiment, signals (e.g., fluorescence intensity) read from all other probes in the array are divided by the signal (e.g., fluorescence intensity) from the control probes thereby normalizing the measurements. Other methods for normalizing gene expression data are known in the art, such as those described, for example, in WO2001/020043 or US 20060136145, each of which is hereby incorporated herein by reference.

Virtually any probe may serve as a normalization control. However, it is recognized that hybridization efficiency varies with base composition and probe length. Preferred normalization probes are selected to reflect the average length of the other probes present in the array, however, they can be selected to cover a range of lengths. The normalization control(s) can also be selected to reflect the (average) base composition of the other probes in the array, however in a preferred embodiment, only one or a few probes are used and they are selected such that they hybridize well (i.e., no secondary structure) and do not match any target-specific probes.

Expression level controls are probes that hybridize specifically with constitutively expressed genes in the biological sample. Virtually any constitutively expressed gene provides a suitable target for expression level controls. Typical expression level control probes have sequences complementary to subsequences of constitutively expressed "housekeeping genes" including, but not limited to the beta-actin gene, the transferrin receptor gene, the GAPDH gene, the HPRT1 gene, and the like. Alternatively or in addition, the expression level controls can be obtained from genes whose expressions are known not to change with AD.

Mismatch controls may also be provided for the probes to the target genes, for expression level controls or for normalization controls. Mismatch controls are oligonucleotide probes or other nucleic acid probes identical to their corresponding test or control probes except for the presence of one or more mismatched bases. A mismatched base is a base selected so that it is not complementary to the corresponding base in the target sequence to which the probe would otherwise specifically hybridize. One or more mismatches are selected such that under appropriate hybridization conditions (e.g., stringent conditions) the test or control probe would be expected to hybridize with its target sequence, but the mismatch probe would not hybridize (or would hybridize to a significantly lesser extent). Preferred mismatch probes contain a central mismatch. Thus, for example, where a probe is a twenty-mer, a corresponding mismatch probe will have the identical sequence except for a single base mismatch (e.g., substituting a G, a C or a T for an A) at any of positions 6 through 14 (the central mismatch).

Mismatch probes thus provide a control for non-specific binding or cross hybridization to a nucleic acid in the sample other than the target to which the probe is directed. Mismatch probes also indicate whether a hybridization is specific or not. For example, if the target is present the perfect match probes should be consistently brighter than the mismatch probes. In addition, if all central mismatches are present, the mismatch probes can be used to detect a mutation. The difference in intensity between the perfect match and the mismatch probe (IBM)-I(MM)) provides a good measure of the concentration of the hybridized material.

In certain embodiments, the obtained expression profile of a biological sample from a subject at risk of AD is compared to a single reference profile (e.g., that of an individual known not to have AD or that of a universal control sample obtained from healthy individuals) to obtain information regarding the phenotype (e.g., positive or negative test of early-stage AD) of the sample being assayed. In yet other embodiments, the obtained expression profile is compared to two or more different reference profiles (e.g., that of individuals known not to have AD or that of two or more universal control samples from healthy individuals) to obtain more in depth information regarding the phenotype of the assayed sample. For example, the obtained expression profile may be compared to a positive and negative reference profile to obtain confirmed information regarding whether the sample has the phenotype of interest (e.g., indications for early-stage AD or being at risk of developing AD).

The comparison of the obtained expression profile and the one or more reference profiles may be performed using any convenient methodology, where a variety of methodologies are known to those of skill in the array art, e.g., by comparing digital images of the expression profiles, by comparing databases of expression data, etc. Patents describing ways of comparing expression profiles include, but are not limited to, U.S. Pat. Nos. 6,308,170 and 6,228,575, the disclosures of which are herein incorporated by reference. Methods of comparing expression profiles are also described above. Patent documents describing various methods or algorithms for obtaining gene expression profiles include, but are not limited to, US20030165952; US20110236903A1; US20110165566A1; US20110098195A1; US20110076685A1; US20100167939A1; US20100112710A1; US20090233297A1; US20090186348A1; US20080171323A1; the disclosures of each of which is hereby incorporated herein by reference. Other methods for analyzing microarray data are well-known in the art including coupled two-way clustering analysis, clustering algorithms (hierarchical clustering, self-organizing maps) and support vector machines. See, e.g., Eisen et al., 95 PROC. NATL. ACAD. SCI. USA 14863-68 (1998); Ermolaeva et al, 20 NATURE GENET. 19-23 (1998); Tamayo et al., 96 PROC. NATL. ACAD. SCI. USA 2907-12 (1999); Getz et al., 97 PROC. NATL. ACAD. SCI. USA 12079-84 (2000); Brown et al., 97 PROC. NATL. ACAD. SCI. USA 262-67 (2000); and Holter et al., 97 PROC. NATL. ACAD. SCI. USA 8409-14 (2000).

The comparison step results in information regarding how similar or dissimilar the obtained expression profile is to the one or more reference profiles, which similarity information is employed to determine the phenotype of the sample being assayed. For example, similarity with a positive control indicates that the assayed sample has a responsive phenotype similar to the responsive reference sample. Likewise, similarity with a negative control indicates that the assayed sample has a non-responsive phenotype to the non-responsive reference sample.

The level of expression of a biomarker (e.g., FKBP1a, FKBP1b, junctophilin 3, junctophilin 4, calmodulin 3, a functional fragment thereof, or a variant thereof) can be further compared to different reference expression levels. For example, a reference expression level can be a predetermined standard reference level of expression in order to evaluate if expression of a biomarker or biomarker set is informative and make an assessment for determining whether the patient tests positive or negative for AD or risk of developing AD. Additionally, determining the level of expression of a biomarker can be compared to an internal reference marker level of expression which is measured at the same time as the biomarker in order to make an assessment for determining whether the patient tests positive or negative for AD or risk of developing AD. For example, expression of a distinct marker panel which is not comprised of biomarkers of the subject technology, but which is known to demonstrate a constant expression level can be assessed as an internal reference marker level, and the level of the biomarker expression is determined as compared to the reference. In an alternative example, expression of the selected biomarkers in a tissue sample which is a non-AD sample can be assessed as an internal reference marker level. The level of expression of a biomarker may be determined as having increased expression in certain aspects. The level of expression of a biomarker may be determined as having decreased expression in other aspects. The level of expression may be determined as no informative change in expression as compared to a reference level. In still other aspects, the level of expression is determined against a pre-determined standard expression level as determined by the methods provided in, for example, WO2012037378, which is hereby incorporated herein by reference.

The subject technology also encompasses kits for detecting the presence of target in a biological sample. For example, the kit can comprise a labeled compound or agent capable of detecting target protein or mRNA in a biological sample; means for determining the amount of target in the sample; and means for comparing the amount of target in the sample with a standard. The compound or agent can be packaged in a suitable container. The kit can further comprise instructions for using the kit to detect target protein or nucleic acid.

2. Prognostic Assays

The assays described herein, such as the preceding diagnostic assays, can be utilized to identify a subject having or at risk of developing AD, MCI or other cognitive impairments. Furthermore, the prognostic assays can be used to determine whether a subject can be administered an agent (e.g., an agonist, antagonist, peptidomimetic, protein, peptide, nucleic acid, small molecule, or other drug candidate) to treat a disease or disorder associated with AD, MCI or other cognitive impairments. For example, such methods can be used to determine whether a subject can be effectively treated with an agent for a disorder such as AD or other cognitive impairments. Thus, the present subject technology provides methods for determining whether a subject can be effectively treated with an agent for a disorder associated with increased or decreased target expression or activity in which a test sample is obtained and target protein or nucleic acid expression or activity is detected (e.g., wherein the abundance of target protein or nucleic acid expression or activity is diagnostic for a subject that can be administered the agent to treat a disorder associated with increased or decreased target expression or activity).

This subject technology is further illustrated by the following examples which should not be construed as limiting. The contents of all references, patents and published patent applications cited throughout this application, are incorporated herein by reference.

EXAMPLES

Example 1

AAV-mediated expression of the Fkbp1b open reading frame (ORF) can counteract $Ca^{2+}$ dyshomeostasis and altered gene expression in the hippocampus of aging rats Methods and Materials Subjects. Studies on adult animals used 3- to 4-month-old male Fischer 344 rats obtained from Harlan. All protocols and procedures were performed in accordance with institutional guidelines and were approved by the Animal Care and Use Committee.

FKBP1b over expression in vivo with adeno-associated virus vectors. To achieve selective expression in vivo, an adeno-associated virus (AAV) vector was used to express Fkbp1b mRNA in vivo. Aged (22 mo) F344 rats received unilateral or bilateral injections of 2 μl of AAV bearing the Fkbp1b construct at a rate of 0.2 μl/min. Following 2-3 weeks of recovery the rats were sacrificed and tissue was utilized for qPCR, immunohistochemistry, slice electrophysiology or microarray analysis. Measures included levels of RNA associated with $Ca^{2+}$ dyshomeostasis, quantification of Fkbp1b, calcium channel and RyR2 protein levels, intracellular measures of the post-burst AHP, accommodation and intracellular $Ca^{2+}$ dynamics. control AAV (AAV titer, 3.56E12 GC) or received no treatment.

Three to 4 weeks after injection, intracellular recordings of the slow after hyperpolarization (sAHP) were obtained from CA1 pyramidal neurons in acute hippocampal slices from both ipsilateral and contralateral sides of nine Fkbp1b-injected animals. Subsequently, qPCR of Fkbp1b was performed on tissue from the dorsal tips and one slice each from both hippocampi of eight of the nine animals studied electrophysiologically. In addition, brains of two other animals unilaterally injected in hippocampus with AAV bearing the Fkbp1b were prepared for immunohistochemical studies.

Microinjection protocol. Under isoflurane anesthesia, rats were placed in a David Kopf Instruments stereotaxic frame. Small holes were drilled in the skull either unilaterally or bilaterally (at points from bregma: posterior, 4.5 mm; lateral, 3.0 mm), and the dura was pierced to allow for microinjection. A Hamilton microsyringe was lowered 1.6 mm into the dorsal hippocampus, a region critical for spatial memory. At the target injection site (CA1 stratum oriens at the peak of the curve of stratum pyramidale), 2 μl of AAV-containing vehicle was delivered at a rate of 0.2 μl/min using a Stoelting QSI microinjection pump. After injection, the syringe was left in place for 5 min, then the small holes in the skull were filled with bone wax, and the incision was sutured. Two to 4 weeks after unilateral microinjections of AAV, rats were killed, and the brains prepared for sectioning and microscopy. See also, Gant et al., 2011.

qPCR. For mRNA quantification, one-step real-time reverse transcription (RT)-PCR was used. RT-PCR amplification was performed as described previously (Chen et al., 2000) using an ABI prism 7700 sequence detection system (Applied Biosystems) and TaqMan One Step RT-PCR reagents (Applied Biosystems). All samples were run in duplicate in a final volume of 50 μl containing 50-100 ng of cellular RNA and a Taq-Man probe (200 μM) and primers (300 nM each) with an amplicon spanning the rat Fkbp1b cDNA region from nucleotides 155 to 259. Cycling parameters for all assays were as follows: 30 min at 48° C., 10 min at 95° C. followed by 40 cycles of 15 s at 95° C., and 1 min at 60° C. Primers were designed using Primer Express software (version 1.5; Applied Biosystems) and chemically synthesized by Applied Biosystems (forward primer, 5'-GCAAGCAGGAAGTCATCAAAGG-3' SEQ ID NO.1; reverse primer, 5'-CAGTAGCTCCATATGCCACATCA-3' SEQ ID NO.2; TaqMan probe, 5'-AGCTCATCTGGGCA-GCGCCTTCTT-3' SEQ ID NO.3). The RNA levels of glyceraldehyde-3-phosphate dehydrogenase were used as normalization controls for RNA quantification.

Patch-clamp recording of $Ca^{2+}$ channel current in cultured neurons. Whole-cell recordings of pharmacologically isolated $Ca^{2+}$ channel currents, using $Ba^{2+}$ as the charge carrier, were obtained from neurons in primary hippocampal cell cultures at 9-12 DW, as described previously (Porter et al., 1997; Blalock et al., 1999; Brewer et al., 2001; Norris et al., 2002). electrophysiological data were acquired at 5-20 kHz using a patch-clamp amplifier (Axopatch 200A), DigiData 1320 digital input/output board and pClamp 7 (Molecular Devices). Cell capacitance measures, membrane resistance, access resistance, and holding current were obtained from the membrane properties function in pClamp7. All cells were held at +70 mV unless stated otherwise. Current-voltage (I-V) relationships were determined by stepping the voltage in increments of 10 mV from 70 to +60 mV for 150 ms. Current was averaged over five traces for each measurement point, and current density was determined by dividing current by cell membrane capacitance (picoamperes per picofarad).

Current-clamp intracellular recording in hippocampal slice pyramidal neurons. Young-adult male F344 rats were anesthetized in a CO2 chamber before rapid decapitation. Our sharp-electrode electrophysiological methods have been described previously (Thibault et al., 2001; Gant et al., 2006). Briefly, intracellular recordings were obtained from CA1 pyramidal neurons in hippocampal slices (350-+m-thick) maintained in oxygenated ACSF (in mM: 128 NaCl, 1.25 KH2PO4, 10 glucose, 26 NaHCO3, 3 KCl, 2 CaCl2, and 2 MgCl2), using sharp glass pipettes filled with HEPES (10 mM), KMeSO4 (2 M), and Calcium Orange tetrapotassium salt (5 mM; Invitrogen). Electrophysiological data were acquired and analyzed using pClamp 8, a sharp-electrode amplifier (Axoclamp 2B), and a DigiData 1320 board (Molecular Devices). Voltage records were digitized at 2-20 kHz and low-pass-filtered at 1 kHz. Input resistance and AHP measures were obtained in current-clamp mode. AHP duration and sAHP amplitude were measured after four Na+ APs triggered by an intracellular depolarizing pulse. The 5 mM concentration of $Ca^{2+}$ indicator used is in a range commonly used in slice imaging experiments (Jaffe et al., 1992; Brown and Jaffe, 1994; Jaffe and Brown, 1994) and apparently does not distort AHP waveforms or obscure aging differences in the AHP (Thibault et al., 2001; Gant et al., 2006).

$Ca^{2+}$ imaging. Methods used were similar to those described previously by several groups (Miyakawa et al., 1992; Brown and Jaffe, 1994; Jaffe and Brown, 1994; Magee and Johnston, 1995; Thibault et al., 2001; Gant et al., 2006). Individual CA1 neurons impaled with sharp pipettes and loaded with the $Ca^{2+}$ indicator Calcium Orange were imaged on the stage of a Nikon E600 microscope equipped with a 40 water immersion objective and a CCD camera (Roper Scientific/Princeton Instruments). Calcium Orange was allowed to diffuse into the cell for at least 10 min before $Ca^{2+}$ fluorescence measures were performed. Calcium Orange was excited using a wavelength switcher (Sutter Instruments Lambda DG-4) and software control (Axon Imaging Workbench; version 2.2.1.54; Molecular Devices). The 575 nm wavelength was monitored through a dichroic mirror centered at 570 nm during excitation with the 550 nm wavelength. The intracellular $Ca^{2+}$ response was elicited by 10 s of 7 Hz repetitive synaptic stimulation (RSS) delivered to the Schaffer collaterals via bipolar stimulation electrode. Stimulation intensity was set at AP threshold and generated an action potential on essentially each pulse (Thibault et al., 2001). $Ca^{2+}$ responses were measured in a region of interest corresponding to the visible outline of the cell soma, excluding surrounding low-intensity diffracted light. Although the central region of the neuron appears brighter (see FIG. 6, inset), this may be related in part to greater indicator loading in this thicker central region of the cell (Tsien, 1988; Nicotera et al., 1994). After background subtraction from an area devoid of cells adjacent to the recorded cell, percentage change in fluorescence was determined relative to baseline (% F/F). Optical sampling rate averaged +5 Hz, which appeared sufficiently sensitive to detect significant changes in the $Ca^{2+}$ response. Excitation of Calcium Orange was essentially continuous during a 10 s train of RSS, but control runs showed that bleaching was minimal (+0.21+0.09% at 5 s RSS; +0.69+0.35% at 10 s RSS; n+7 cells). The ryanodine-sensitive component (CICR component) of the $Ca^{2+}$ response was determined by subtracting the post-ryanodine $Ca^{2+}$ response from the pre-ryanodine response [(pre-ryanodine % ΔF/F)–(post-ryanodine % ΔF/F)=ryanodine sensitive component].

Statistical analyses. Data analysis was performed with Clampfit8(Molecular Devices), and statistical analysis was performed with Stat-View (SAS Institute). Variables were analyzed using ANOVA across all groups with means and SEs reported. Fisher's protected least significant difference (PLSD) test was used for post hoc group comparisons. p values +0.05 were considered significant.

This microinjection results in overexpression of FKBP1b mRNA and protein (confirmed by qPCR and immunohistochemistry). The electrophysiological effects of unilateral microinjection into one hippocampus of aging rats of adeno-associated viral (AAV) vector containing the open reading frame (ORF) of the Fkbp1b gene is shown in FIG. 1. The quantitative group measures (mean+/−SEM) of intracellular electrode recordings of membrane voltage responses that are well-established to vary in magnitude with the amount of calcium released by intracellular ryanodine receptors (see Gant et al, 2006). As shown in FIG. 1, the voltage responses obtained in this study are the amplitude of the calcium-dependent medium afterhyperpolarization (mAHP)(top panel), amplitude of the calcium-dependent slow afterhyperpolarization (sAHP)(middle panel), and duration of the calcium-dependent slow afterhyperpolarization (sAHP) (bottom panel). The data reveal significant differences in these responses in neurons recorded from the viral vector-injected hippocampus vs. those recorded from the control (non-injected) hippocampus, such that the injected-side neurons exhibit a younger phenotype (lesser magnitude). Larger amplitude AHPs develop with aging and have been correlated with impaired memory.

These results show that the AAV microinjections impact several biotargets of aging rats, indicating that calcium release-stabilizing molecules such as FKBPs are novel therapeutic agents and/or targets for interventions aimed at protection against unhealthy brain aging or Alzheimer's disease.

Example 2

FKBP1b Overexpression and Reversal of Aging Biomarkers

Figure 3:
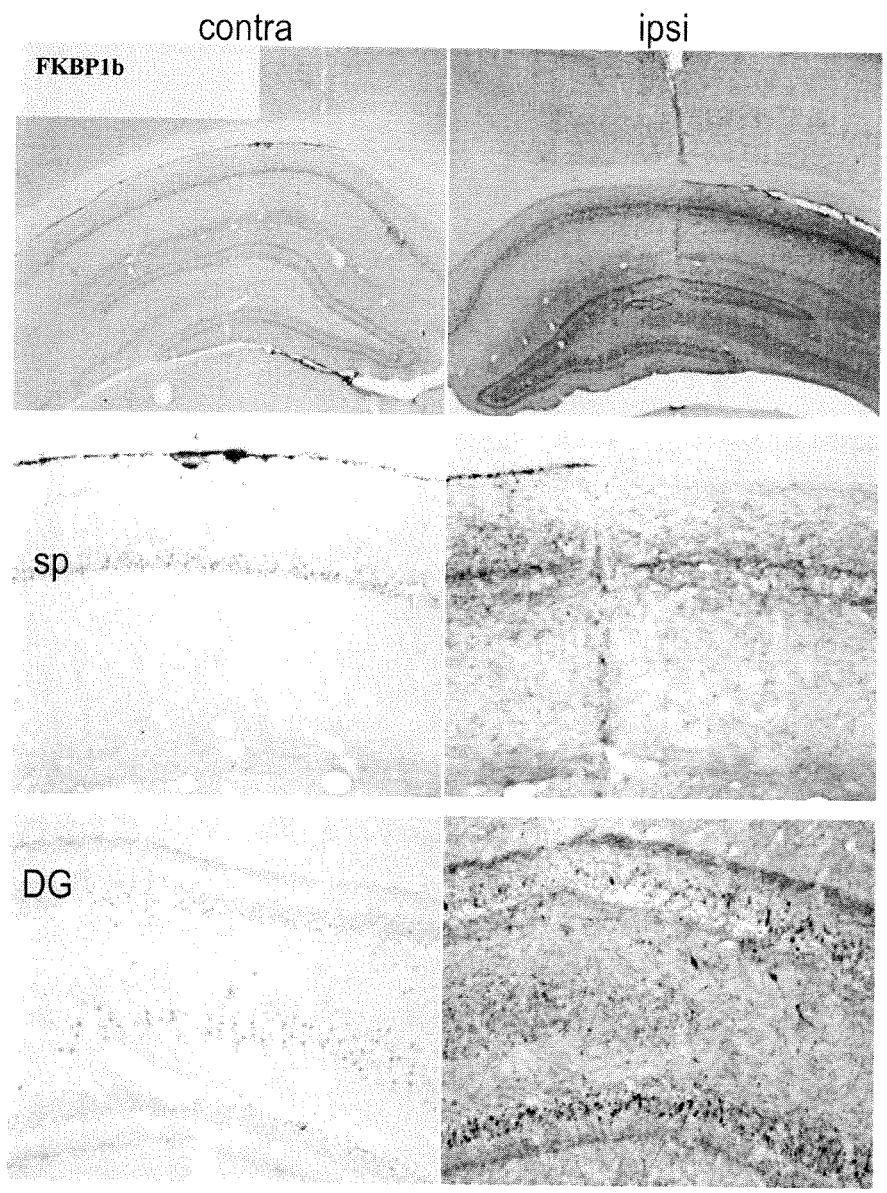
FIG. 3 shows the AAV-ORF-mediated overexpression of FKBP1b/12.6 validated at the protein level. In vivo direct microinjection of AAV with Fkbp1b ORF into one hippocampus (ipsilateral-ipsi) dramatically increased FKBP1b expression compared to the non-injected contralateral hippocampus (contra). Note more intense immunohistochemical staining of FKBP1b/12.6 throughout ipsilateral hippocampus (ipsi) (upper panel). More intense staining is also shown at higher magnification in the CA stratum pyramidale (sp) layer (middle panel) and dentate gyrus (DG) (lower panel).

The aim of this study was to determine whether AAV-mediated overexpression of the Fkbp1b open reading frame (ORF) can reverse hippocampal $Ca^{2+}$ dyshomeostasis and cognitive impairment in aging rats. Aged (22 mo) F344 rats received unilateral or bilateral injections of 2 µl of AAV bearing the Fkbp1b ORF construct or empty AAV vector control. IHC and qPCR analyses revealed substantial upregulated FKBP1b in hippocampal sites of AAV-ORF injection. See FIG. 3.

Figure 4:
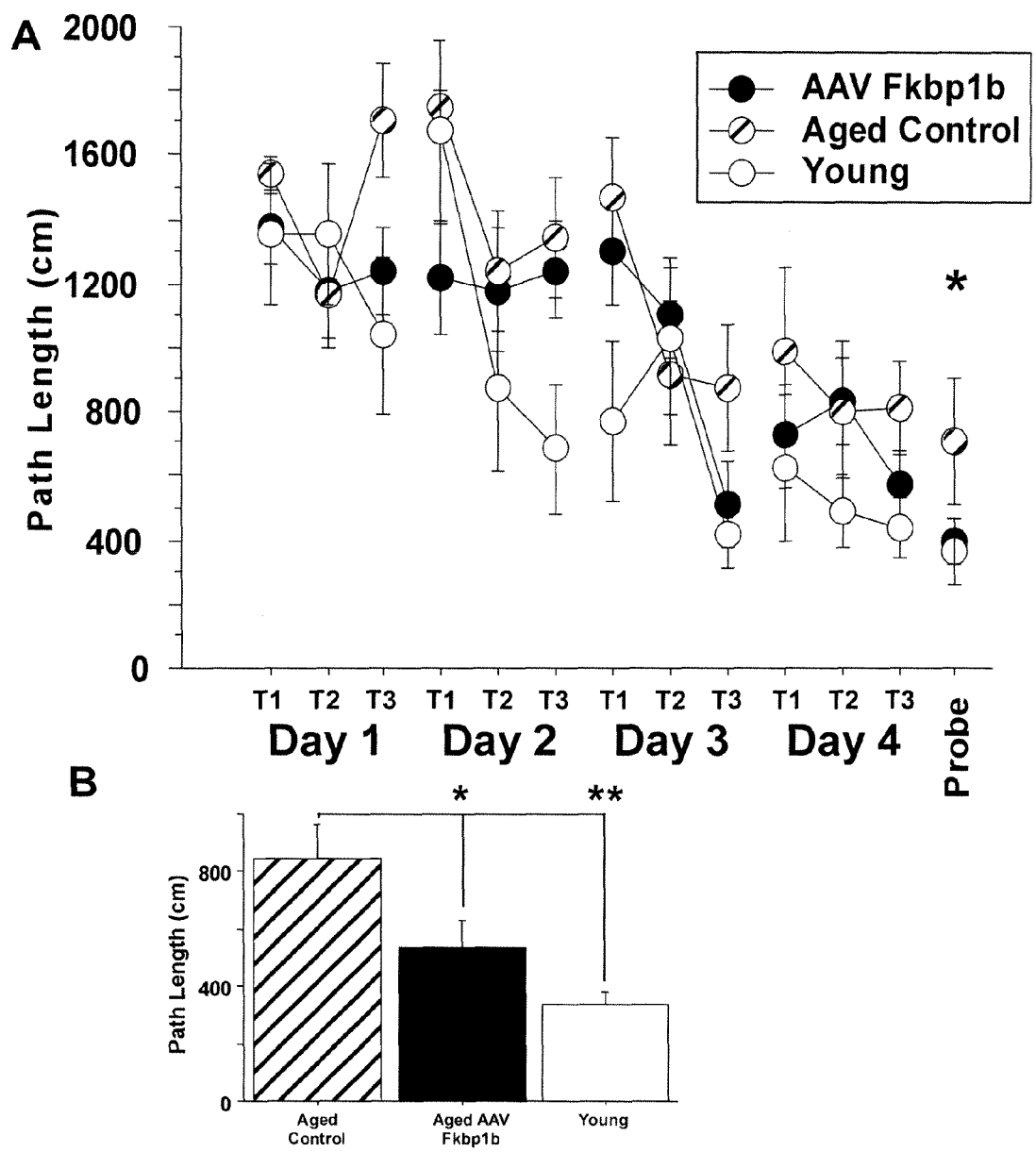
FIG. 4 shows the reversal of Spatial Water Maze Learning Deficit in Aged Rats by Hippocampal Microinjection of Adeno-Associated Viral (AAV) Vectors Expressing FKBP1b. Panel A is a graph of the water maze learning performance of 3 groups of F344 rats, presented as the path length (distance in cm) traveled to find the submerged escape platform during 12 training trials and one probe (retention) test (Shorter path length=better learning). The groups consisted of Aged Controls (22 mo), Aged AAV-Fkbp1b injected (22 mo) and Young-Adult Controls (4 mo). The aged AAV-Fkbp1b group received bilateral infusions of AAV expressing the Fkbp1b open reading frame. The other two groups received infusions of control AAV expressing only green fluorescing protein. Rats were trained by giving three learning trials/day over 4 days. On the fifth day a probe test was conducted with the escape platform missing to measure memory retention. Young Controls and Aged-Fkbp1b-treated animals performed significantly better than Aged Controls on the retention test and on the final two days of training. Panel B is the average path length on the 3rd training trial of the 3rd and 4th training days. The Aged AAV-Fkbp1b group and the Young group performed significantly better than Aged controls. (*=$p<0.05$'**=$p<0.001$).

Following 4-5 weeks, the rats were tested on a spatial water maze, after which hippocampal tissue was utilized for slice electrophysiology, and qPCR, immunohistochemistry or microarray analysis. Results showed that the AAV-ORF microinjections reversed electrophysiological and behavioral biomarkers of aging in rats. More importantly, it was determined that overexpression of FKBP1b in hippocampus of aged rats improved memory and maze learning. See FIG. 4. These results show that calcium release-stabilizing molecules such as FKBPs can be used as therapeutic agents for treatment of age-related cognitive malfunctions.

Those skilled in the art will recognize, or be able to ascertain using no more than routine experimentation, many equivalents to the specific embodiments of the subject technology described herein. Such equivalents are intended to be encompassed by the following claims. The results indicate that of other forms without departing from the spirit thereof. The accompanying claims and their equivalents are intended to cover such forms or modifications as would fall within the scope and spirit of the subject technology. The contents of all references, patents and published patent applications cited throughout this application, are incorporated herein by reference.

SEQUENCE LISTING

```
<160> NUMBER OF SEQ ID NOS: 3

<210> SEQ ID NO 1
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
gcaagcagga agtcatcaaa gg                                              22

<210> SEQ ID NO 2
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
cagtagctcc atatgccaca tca                                             23

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 3
agctcatctg ggcagcgcct tctt                                            24
```

The foregoing description is provided to enable a person skilled in the art to practice the various embodiments described herein. While the subject technology has been particularly described with reference to the various figures and configurations, it should be understood that these are for illustration purposes only and should not be taken as limiting the scope of the subject technology.

Furthermore, to the extent that the term "include," "have," or the like is used in the description or the claims, such term is intended to be inclusive in a manner similar to the term "comprise" as "comprise" is interpreted when employed as a transitional word in a claim.

The word "exemplary" is used herein to mean "serving as an example, instance, or illustration." Any embodiment described herein as "exemplary" is not necessarily to be construed as preferred or advantageous over other embodiments.

While certain aspects and embodiments of the subject technology have been described, these have been presented by way of example only, and are not intended to limit the scope of the subject technology. Indeed, the novel methods and systems described herein may be embodied in a variety

What is claimed is:

1. A method of treating Alzheimer's Disease (AD), early-stage AD, mild cognitive impairment (MCI), or other forms of age-related cognitive decline in a subject in need thereof, comprising administering to the subject by way of injection or infusion into brain tissue that is affected by AD, early-stage AD, MCI or age-related cognitive decline, a replication-defective viral expression vector comprising a polynucleotide sequence that encodes at least one of FKBP1a or FKBP1b, or a polynucleotide having at least about 60% sequence identity over its entire length to at least one of FKBP1a, FKBP1b, or both and encoding a polypeptide having calcium release inhibiting activity on ryanodine receptors (RyRs), said polynucleotide sequence being operably linked to a promoter sequence, wherein expression of the at least one of FKBP1a or FKBP1b, or the polynucleotide having at least about 60% sequence identity over its entire length to at least one of FKBP1a, FKBP1b, or both, in the brain tissue of the subject results in reduced calcium-release from RyRs in the brain tissue of the subject and reduces cognitive impairment of the subject.

2. The method of claim 1, wherein the replication-defective viral expression vector is an adeno-associated expression vector.

3. The method of claim 1, wherein the replication-defective viral expression vector comprises a polynucleotide encoding FKBP1b.

4. The method of claim 1 wherein the polynucleotide encodes FKBP1a.

5. The method of claim 2 wherein the replication-defective viral expression vector is injected or infused into the hippocampus of the subject.

6. A method of treating Alzheimer's Disease (AD), early-stage AD, mild cognitive impairment (MCI), or other forms of age-related cognitive decline in a subject in need thereof, comprising administering to the subject by way of injection or infusion into brain tissue that is affected by AD, early-stage AD, MCI or age-related cognitive decline, a replication-defective viral expression vector comprising a polynucleotide sequence that encodes at least one of FKBP1a or FKBP1b, said polynucleotide sequence being operably linked to a promoter sequence, wherein expression of the FKBP1a, FKBP1b, or both in the brain tissue of the subject results in reduced calcium-release from ryanodine receptors in the brain tissue of the subject and reduces cognitive impairment of the subject.

7. The method of claim 6, wherein the replication-defective viral expression vector is an adeno-associated expression vector.

8. The method of claim 6, wherein the replication-defective viral expression vector comprises a polynucleotide encoding FKBP1b.

9. The method of claim 6 wherein the polynucleotide encodes FKBP1a.

10. The method of claim 6 wherein the replication-defective viral expression vector is injected or infused into the hippocampus of the subject.

* * * * *